(12) United States Patent
Oobayashi et al.

(10) Patent No.: US 11,978,004 B2
(45) Date of Patent: May 7, 2024

(54) INTELLECTUAL PRODUCTIVITY EVALUATION DEVICE AND INTELLECTUAL PRODUCTIVITY EVALUATION METHOD

(71) Applicant: PANASONIC INTELLECTUAL PROPERTY MANAGEMENT CO., LTD., Osaka (JP)

(72) Inventors: Fumiaki Oobayashi, Aichi (JP); Hiroshi Shimoda, Kyoto (JP); Hirotake Ishii, Kyoto (JP); Shota Shimonaka, Tokyo (JP); Kimi Ueda, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 517 days.

(21) Appl. No.: 16/607,699

(22) PCT Filed: Apr. 20, 2018

(86) PCT No.: PCT/JP2018/016229
§ 371 (c)(1),
(2) Date: Oct. 23, 2019

(87) PCT Pub. No.: WO2018/198948
PCT Pub. Date: Nov. 1, 2018

(65) Prior Publication Data
US 2020/0143308 A1    May 7, 2020

(30) Foreign Application Priority Data
Apr. 24, 2017  (JP) .................. 2017-085369

(51) Int. Cl.
*G09B 19/00*    (2006.01)
*A61B 5/16*    (2006.01)
*G06Q 10/0639*    (2023.01)

(52) U.S. Cl.
CPC ....... *G06Q 10/06393* (2013.01); *A61B 5/162* (2013.01); *A61B 5/168* (2013.01)

(58) Field of Classification Search
None
See application file for complete search history.

(56) References Cited

U.S. PATENT DOCUMENTS 7,295,124 B2    11/2007  Guillen
2003/0200043 A1    10/2003  Wen et al.
(Continued)

FOREIGN PATENT DOCUMENTS

JP    2001-120522 A    5/2001
JP    2002-140429 A    5/2002
(Continued)

OTHER PUBLICATIONS

Communication pursuant to Article 94(3) EPC, issued in European Patent Application No. 18 792 222.4, dated Jan. 3, 2022.
(Continued)

*Primary Examiner* — James B Hull
(74) *Attorney, Agent, or Firm* — Rimon P.C.

(57) ABSTRACT

An intellectual productivity evaluation device includes: an obtainment unit configured to obtain a set of answer times required by a subject to accomplish a task of answering a plurality of questions, the task being imposed on the subject as intellectual work; an evaluation unit configured to calculate an evaluation value related to a depth of concentration of the subject in a concentrated state using the set of answer times obtained by the obtainment unit based on a model in which the subject is in the concentrated state or an uncon-
(Continued)

centrated state during the intellectual work; and an output unit configured to output evaluation value information indicating the evaluation value calculated by the evaluation unit.

10 Claims, 12 Drawing Sheets

(56) References Cited

U.S. PATENT DOCUMENTS

| | | |
|---|---|---|
| 2004/0186765 A1 | 9/2004 | Kataoka |
| 2005/0053904 A1 | 3/2005 | Shephard et al. |
| 2005/0191609 A1 | 9/2005 | Fadel et al. |
| 2006/0074340 A1 | 4/2006 | Murata |
| 2011/0151425 A1 | 6/2011 | Smith et al. |
| 2015/0154523 A1 | 6/2015 | Oobayashi et al. |
| 2015/0317592 A1 | 11/2015 | Oobayashi et al. |
| 2016/0334121 A1 | 11/2016 | Oobayashi |
| 2017/0188926 A1* | 7/2017 | Obayashi ............... A61B 5/168 |
| 2018/0169476 A1 | 6/2018 | Shimada et al. |

FOREIGN PATENT DOCUMENTS

| | | | | |
|---|---|---|---|---|
| JP | 2005-070169 A | | 3/2005 | |
| JP | 2014-063128 A | | 4/2014 | |
| JP | 2014-186289 A | * | 10/2014 | ............ G09B 19/00 |
| TW | 201700064 A | | 1/2017 | |
| TW | 201807675 A | | 3/2018 | |
| WO | 2015/182032 A1 | | 12/2015 | |

OTHER PUBLICATIONS

Extended European Search Report dated Mar. 11, 2020 issued for the corresponding EP patent application No. 18792222.4.
Ishii, H. et al., "Intellectual productivity under task ambient lighting," Lighting Research and Technology, 2016, 0; 1-16.
Miyagi, K. et al., "Development of an Evaluation Method for Office Work Productivity," Springer-Verlag Berlin Heidelberg 2009, pp. 101-110.
International Search Report and Written Opinion dated Jul. 10, 2018 in International Application No. PCT/JP2018/016229; with partial English translation.

* cited by examiner

INTELLECTUAL PRODUCTIVITY EVALUATION DEVICE AND INTELLECTUAL PRODUCTIVITY EVALUATION METHOD

CROSS-REFERENCE OF RELATED APPLICATIONS

This application is the U.S. National Phase under 35 U.S.C. § 371 of International Patent Application No. PCT/JP2018/016229, filed on Apr. 20, 2018, which in turn claims the benefit of Japanese Application No. 2017-085369, filed on Apr. 24, 2017, the entire disclosures of which Applications are incorporated by reference herein.

TECHNICAL FIELD

The present disclosure relates to an intellectual productivity evaluation device and an intellectual productivity evaluation method.

BACKGROUND ART

Various methods of evaluating the intellectual productivities of subjects are known. For example, PTL1 discloses an intellectual productivity analyzing device that causes a subject to answers a plurality of questions to analyze the degree of concentration of the subject based on the answer time. The intellectual productivity analyzing device described in PTL1 calculates, as an evaluation value indicating the intellectual productivity, the percentage of the time of concentration to the measured answer time.

CITATION LIST

Patent Literature

PTL 1: Japanese Unexamined Patent Application Publication No. 2014-186289

SUMMARY

Technical Problem

Human living space environment is controlled utilizing an air conditioner or a lighting system. At this time, the intellectual productivity of a subject can be evaluated under controlled environment utilizing the intellectual productivity analyzing device described in PTL1. It is however impossible to improve the efficiency of the operation of the system controlling the environment.

To address the problem, it is an objective of the present disclosure to provide an intellectual productivity evaluation device and an intellectual productivity evaluation method that support an improvement in the efficiency of the operation of the system.

Solutions to Problems

In order to achieve the objective, an intellectual productivity evaluation device according to one aspect of the present disclosure includes: an obtainment unit configured to obtain a set of answer times required by a subject to accomplish a task of answering a plurality of questions, the task being imposed on the subject as intellectual work; an evaluation unit configured to calculate an evaluation value related to a depth of concentration of the subject in a concentrated state using the set of answer times obtained by the obtainment unit, based on a model in which the subject is in the concentrated state or an unconcentrated state during the intellectual work; and an output unit configured to output evaluation value information indicating the evaluation value calculated by the evaluation unit.

According to another aspect of the present disclosure, an intellectual productivity evaluation method includes: obtaining a set of answer times required by a subject to accomplish a task of answering a plurality of questions, the task being imposed on the subject as intellectual work; calculating an evaluation value related to a depth of concentration of the subject in a concentrated state using the set of answer times obtained based on a model in which the subject is in the concentrated state or an unconcentrated state during the intellectual work; and outputting evaluation value information indicating the evaluation value calculated.

According to further another aspect, the present disclosure is implemented by a program that causes a computer to execute the intellectual productivity evaluation method. Alternatively, the present disclosure may be implemented by a computer-readable recording medium storing the program.

Advantageous Effect

The intellectual productivity evaluation device and the intellectual productivity evaluation method according to the present disclosure support an improvement in the efficiencies of the operations of systems.

DESCRIPTION OF EXEMPLARY EMBODIMENT

An intellectual productivity evaluation device, an intellectual productivity evaluation method, and other aspects according to an embodiment of the present disclosure will be described below in detail with reference to the drawings. Note that the embodiment described below is a mere preferred specific example of the present disclosure. The numerical values, shapes, materials, constituent elements, the arrangement and connection of the constituent elements, steps, step orders etc. shown in the following embodiment are thus mere examples and are not intended to limit the scope of the present disclosure. Among the constituent elements in the following embodiment, those not recited in any of the independent claims defining the broadest concept of the present disclosure are described as optional constituent elements.

Each figure is a schematic view and not necessarily strictly illustrated. The scales are thus not necessarily identical among the figures. In the figures, substantially the same constituent elements are assigned with the same reference marks, and redundant descriptions will be omitted or simplified.

EMBODIMENT

Outline

Figure 1:
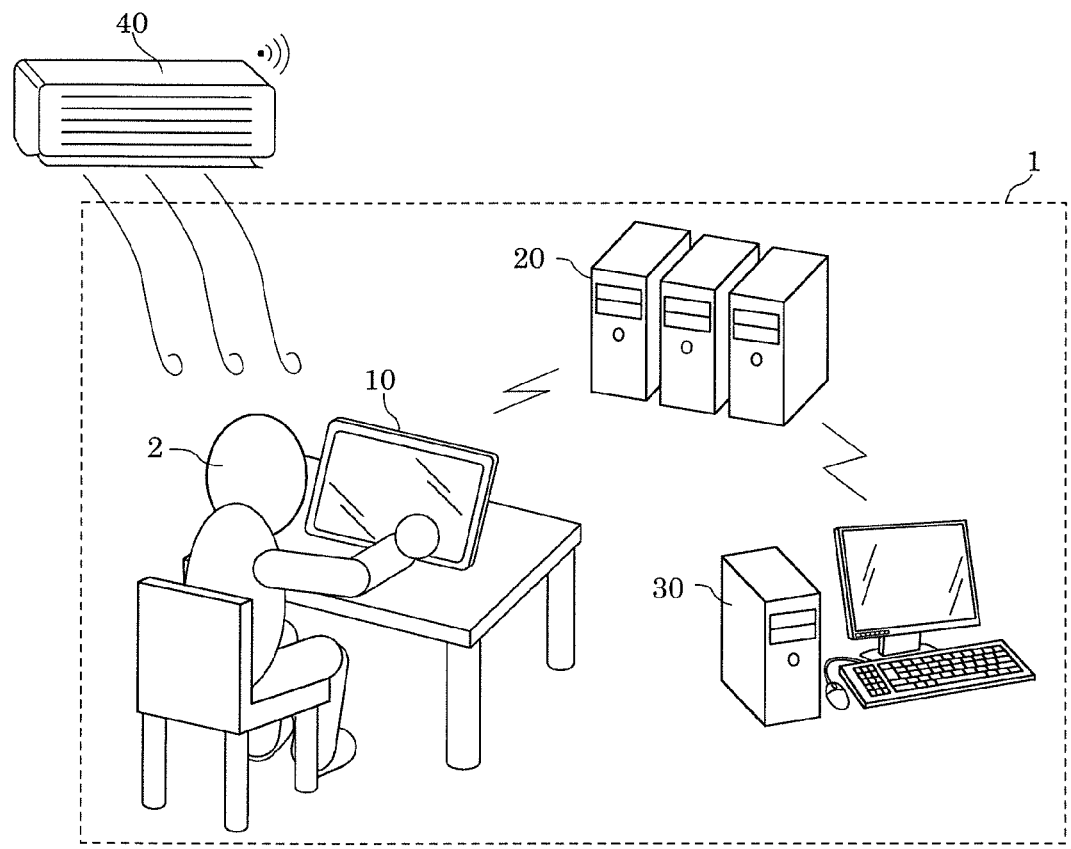
FIG. 1 illustrates a configuration of an intellectual productivity evaluation system according to an embodiment.

First, the outline of an intellectual productivity evaluation system according to this embodiment will be described with reference to FIG. 1. FIG. 1 illustrates a configuration of intellectual productivity evaluation system 1 according to this embodiment.

Intellectual productivity evaluation system 1 is a system evaluating the intellectual productivity of subject 2. Intellectual productivity evaluation system 1 causes subject 2 to do intellectual work to evaluate the intellectual productivity of subject 2. The intellectual work is, for example, answering a plurality of questions.

As shown in FIG. 1, intellectual productivity evaluation system 1 includes operation terminal 10, data collection device 20, and intellectual productivity evaluation device 30. Operation terminal 10 presents the plurality of questions to subject 2 and receives inputs of answers to the presented questions from subject 2. Data collection device 20 obtains, from operation terminal 10, answer times required by subject 2 to answer the questions. Intellectual productivity evaluation device 30 evaluates the intellectual productivity of subject 2 using a set of answer times obtained by data collection device 20. Specifically, intellectual productivity evaluation device 30 calculates an evaluation value related to the "depth" of concentration of subject 2 on the intellectual work to evaluate the intellectual productivity of subject 2.

Intellectual productivity evaluation device 30 outputs evaluation value information indicating the calculated evaluation value. The evaluation value information is output to a control unit of system 40 such as an air conditioner. The control unit controls system 40 based on the evaluation value information to create environment that facilitates the concentration of subject 2. Under the environment that facilitates the concentration, the work efficiency of subject 2 improves, which leads to a decrease in the work time. A reduction in the work time reduces the operation time of system 40, resulting in lower energy consumption. In this manner, intellectual productivity evaluation device 30 according to this embodiment outputs the evaluation value information to support an improvement in the efficiency of the operation of system 40.

First, the definition of the intellectual productivity in this specification and how to evaluate the intellectual productivity will be described below, including how the present disclosure was made. The detail of constituent elements of intellectual productivity evaluation system 1 will be described later.

Intellectual Productivity

In this specification, the intellectual productivity means the amount of intellectual work per unit time. In short, the intellectual productivity corresponds to the efficiency of the intellectual work.

Conventionally, the intellectual productivity has been evaluated based on various methods such as (a) subjective evaluation, (b) evaluation using a physiological index, (c) evaluation on work performance for a virtual task, and (d) evaluation using a concentration index. However, the methods (a) to (d) have the following problems.

For example, (a) the subjective evaluation can be easily performed by a questionnaire survey, for example. However, this method is largely affected by individual feeling differences and less objective.

The evaluation (b) using a physiological index is performed by measuring physiological signals such as brain waves or a heart rate of a working subject and thus exhibits high temporal resolution and evaluation objectivity. However, this method requires a dedicated apparatus for measurement and a long time for the measurement per target. There are also unclear points in the relationship between the physiological signals and the work efficiency. This method is thus insufficient to evaluate intellectual productivity.

The evaluation (c) on the work performance for a virtual task causes a subject to do a task, such as text typing, to measure the work efficiency and is thus highly objective. However, the subject becomes skilled at the work after repetitive tasks and the work efficiency improves. Due to this learning effect, it becomes difficult to extract only the intellectual productivity for the purpose of evaluation.

The evaluation (d) using a concentration index focuses on the fact that a person needs to allocate his/her cognitive resources to certain intellectual work and pay attention. This method is specifically described in PTL1. PTL1 is based a model using three states of "working," "short break," and "long break" during intellectual work of a person. In the model, the "working" state and the "short break" are referred to as a "concentrated" state, whereas the "long break" is referred to as an "unconcentrated" state. The ratio of the time of concentration in which the subject is concentrated to the measurement time is then calculated as an index.

The evaluation using a concentration index allows objective and quantitative evaluation on concentration. However, this method fails to evaluate the quality of concentration. The present inventors found that the quality of concentration differs even when the subject is concentrated. Specifically, the present inventors found that a concentrated state cannot be collectively considered and includes a plurality of states.

Based on the findings, the present inventors have devised an intellectual productivity evaluation system, focusing on the evaluation (d) capable of objective and quantitative evaluation using a concentration index. Intellectual productivity evaluation system 1 according to this embodiment objectively and quantitatively evaluates the quality of concentration of subject 2 based on a concentration model according to the quality of concentration.

Concentration Model

Next, a concentration model according to this embodiment will be described.

In this specification, "concentration" corresponds to allocation of cognitive resources to a work target. "Cognitive resources" are resources, such as attention or recognition, requiring a person to use the brain. Each person has a certain amount of cognitive resources.

The human allocates cognitive resources to intellectual work to do the intellectual work. Allocation of a large amount of cognitive resources to the intellectual work leads to completion of the intellectual work in a short time. That is, while allocating a large amount of cognitive resources, the person can be regarded to as being "deeply concentrated."

In this specification, how to allocate the cognitive resources is defined by "depth of concentration." The "depth of concentration" indicates a person's degree of concentration and is an evaluation index of the quality of concentration.

Figure 2:
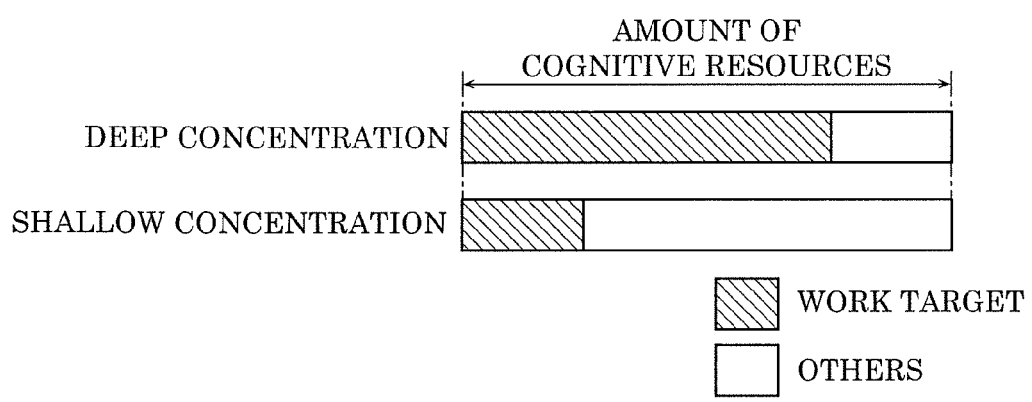
FIG. 2 illustrates a relationship between how a person allocates cognitive resources and the person's depth of concentration.

FIG. 2 illustrates a relationship between how a person allocates his/her cognitive resources and the person's depth of concentration. As shown in FIG. 2, the person allocates a great part of a certain amount of resources to work when deeply concentrated. On the other hand, the person allocates a smaller part of the certain amount of resources when less deeply concentrated.

Figure 3:
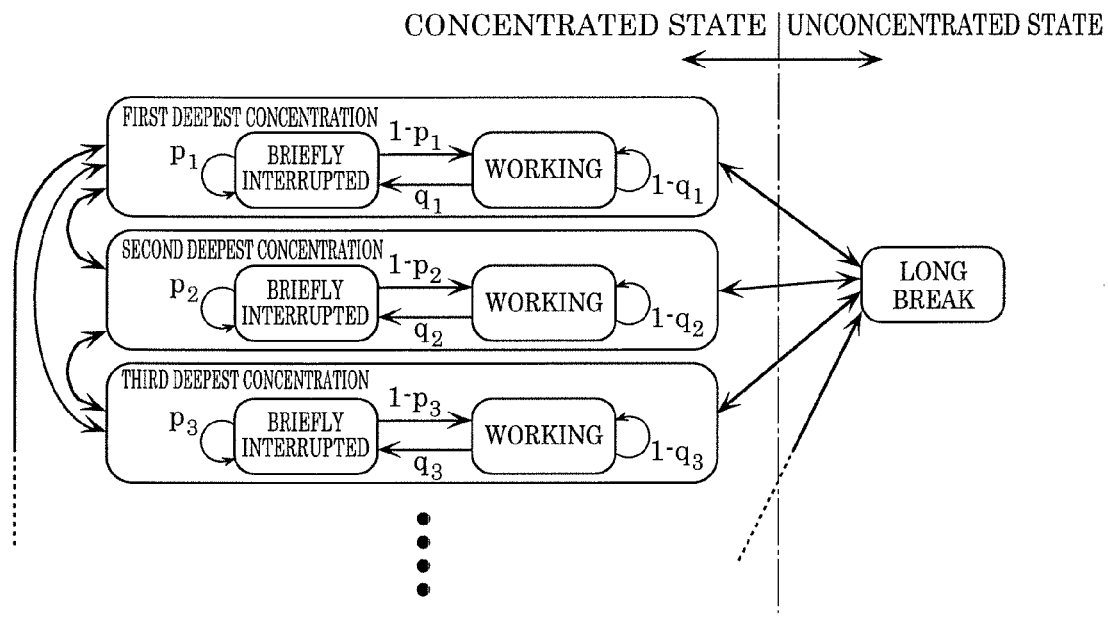
FIG. 3 is a state transition diagram illustrating a concentration model in view of the person's depth of concentration.

FIG. 3 is a state transition diagram illustrating a concentration model in view of the person's depth of concentration.

In the concentration model shown in FIG. 3, a "concentrated state" is the state where the person allocates his/her cognitive resources to a work target and a mixture of a "briefly interrupted" state and a "working" state. When "briefly interrupted," the person pays attention to the work target but the work is unconsciously interrupted, that is, what is called "blocked." While "working," the person pays attention to the work target and the work actually progresses.

An "unconcentrated state" is the state where the person intentionally has a break, specifically, a "long break" without allocating his/her cognitive resources to the work target. During the "long break," the person consciously stops the work without paying attention to the work target due to fatigue, for example.

As shown in FIG. 3, the concentrated state includes a plurality of gradual concentration levels depending on the depth of concentration. Specifically, the concentrated state includes n concentration levels of: the first deepest concentration, the second deepest concentration, the third deepest concentration, . . . , and the n-th deepest concentration in descending order of depth of concentration. Note that n is a natural number of two or more.

In the concentration model, transitions occur among the plurality of states including the concentration levels such as the first deepest concentration and the second deepest concentration as well as the unconcentrated state, at a certain transition probability. Specifically, the transition probabilities of the respective states in the concentration model form a certain Markov model. In FIG. 3, bidirectional arrows between the states indicate the transitions between the states.

In the "deepest concentration," the person allocates almost all the cognitive resources to a work target. In the first deepest concentration, subject 2 is most deeply concentrated among his/her possible concentration levels. That is, the subject is more deeply concentrated in the first deepest concentration than in the second deepest concentration. The first deepest concentration corresponds to the state where the subject is deprived of attention by none of elements, such as the ambient environment and fatigue, but the work target. For example, subject 2 is most concentrated when focusing on his/her entire attention to the work and being deeply into the work.

In the "second deepest concentration," the person allocates a part of the cognitive resources to an element other than the work target. In the second deepest concentration, subject 2 is second most deeply concentrated among his/her possible concentration levels. That is, in the second deepest concentration, the subject is less deeply concentrated than in the first deepest concentration, and more deeply concentrated than at the concentration levels other than the first deepest concentration. The second deepest concentration corresponds to the state where the subject is deprived of attention by an external cause or intentionally limits the cognitive resources to be allocated to the work target.

Each of the first deepest concentration and the second deepest concentration is the mixture of the working state and the briefly interrupted state. Specifically, at these concentration levels, the Markov model is established which represents certain transition probabilities between the working state and the briefly interrupted state.

As shown in FIG. 3, in the first deepest concentration, $p_1$ represents the probability of repeating the briefly interrupted state, $1-p_1$ the probability of transitioning from the briefly interrupted state to the working state, $q_1$ the probability of transitioning from the working state to the briefly interrupted state, and $1-q_1$ the probability of repeating the working state. The same applies to the second deepest concentration and the other concentration levels.

The third deepest or shallower concentration shown in FIG. 3 represents the state where the subject allocates little of the cognitive resources to the work target and is distracted from the work, that is, deprived of attention by an external cause. This can be substantially equated to a long break. Intellectual productivity evaluation system 1 according to this embodiment employs a concentration model including, as the concentrated state, only the first deepest concentration and the second deepest concentration.

Configuration

Now, a configuration of intellectual productivity evaluation system 1 according to this embodiment will be described.

In this embodiment, operation terminal 10, data collection device 20, and intellectual productivity evaluation device 30 are dedicated devices or general-purpose computers configured independently from each other. The general-purpose computers are, for example, laptop or desktop computers, tablet terminals, smartphone, game consoles or devices. As shown in FIG. 1, data collection device 20 receives and sends information to and from operation terminal 10 and intellectual productivity evaluation device 30 via wired or wireless communication networks.

Intellectual productivity evaluation system 1 may be a single integrated computer. For example, a single tablet terminal or a smartphone may function as operation terminal 10, data collection device 20, and intellectual productivity evaluation device 30.

Figure 4:
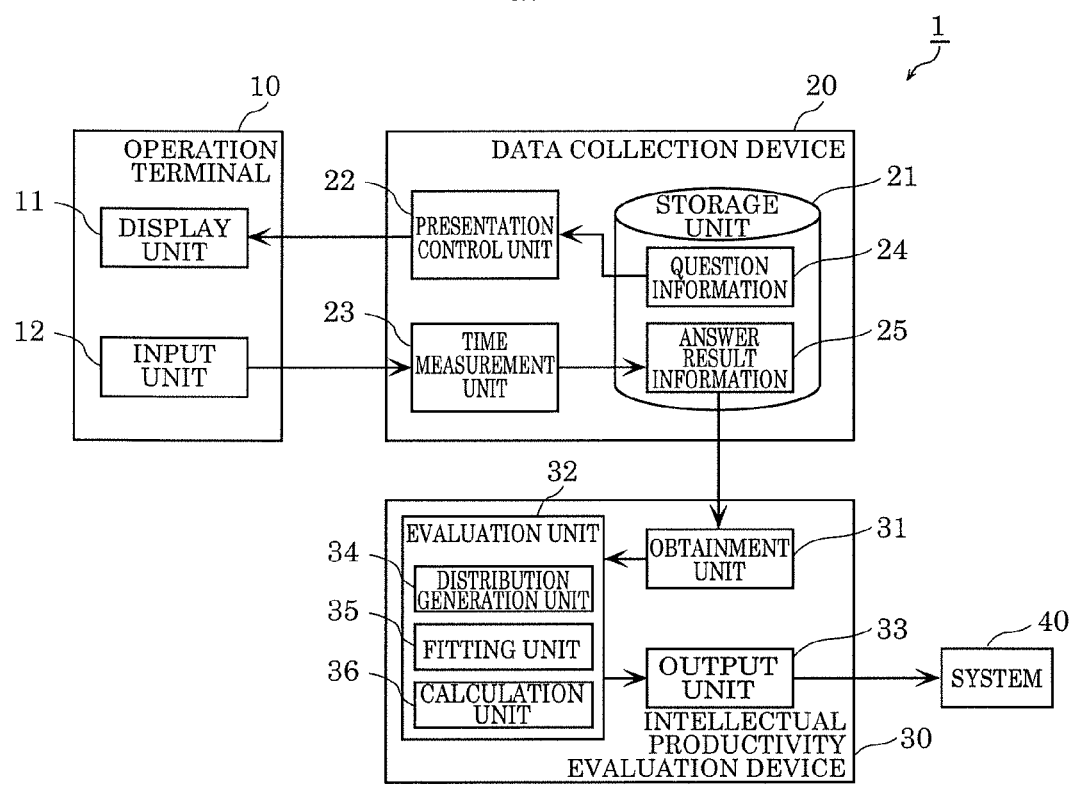
FIG. 4 is a block diagram illustrating a functional configuration of the intellectual productivity evaluation system according to the embodiment.

Now, functional configurations of operation terminal 10, data collection device 20, and intellectual productivity evaluation device 30 will be described with reference to FIG. 4. FIG. 4 is a block diagram illustrating a functional configuration of intellectual productivity evaluation system 1 according to this embodiment.

Operation Terminal

Operation terminal 10 aims to cause subject 2 to do intellectual work. Specifically, operation terminal 10 presents a plurality of questions to subject 2, and receives inputs of answers to the presented questions. As shown in FIG. 4, operation terminal 10 includes display unit 11 and input unit 12. Although not shown in the figure, operation terminal 10 also includes a communication unit for communicating with data collection device 20. The communication unit establishes, for example, wireless communications with data collection device 20.

Display unit 11 presents the plurality of questions to subject 2. Specifically, display unit 11 sequentially displays the plurality of questions one by one. This facilitates measurement of the answer times for the respective questions, which will be described later. Display unit 11 obtains the questions sent from data collection device 20 and displays the obtained questions. Display unit 11 may be, for example, a liquid crystal display device or an electroluminescence (EL) display device but is not limited thereto.

Display unit 11 may collectively display the plurality of questions. In this case, the time from the collective display to the reception of a first answer may be regarded as the answer time for the first question and the times from subsequent answers to the next answers as answer times to measure the answer times.

Input unit 12 receives the answers from subject 2. For example, input unit 12 may be a touch sensor or hardware keys. For example, display unit 11 and input unit 12 may be touch panel displays. Input unit 12 sends the received answers to data collection device 20.

In this embodiment, the plurality of questions are at the same difficulty level requiring skills used at office work. Specifically, the questions require language processing skills, mathematical processing skills, and comparative judgement skills.

Figure 5:
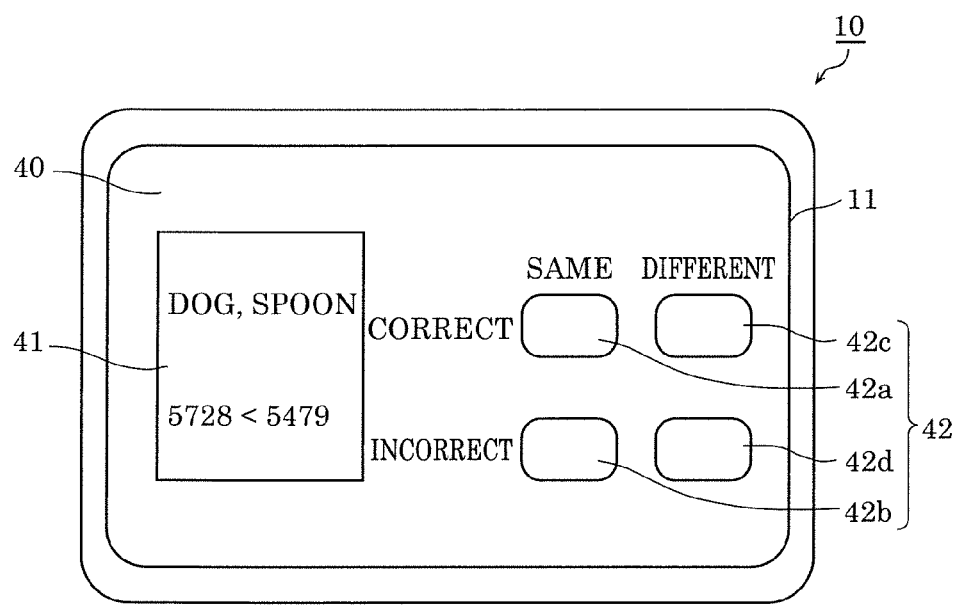
FIG. 5 illustrates an example of questions to be answered by a subject on the intellectual productivity evaluation system according to the embodiment.

FIG. 5 illustrates an example of questions 41 to be answered by subject 2 on intellectual productivity evaluation system 1 according to this embodiment. As shown in FIG. 5, display unit 11 of operation terminal 10 displays question screen 40 including questions 41 and answer button group 42.

Questions 41 are, for example, comparison questions. Specifically, the comparison questions are to be answered whether the meaning categories of two terms are the same or different and whether the combination between two numbers and the magnitude relation is correct or incorrect. As questions 41 shown in FIG. 5, two terms of "dog" and "spoon" and two numbers of "5728" and "5479" are displayed. In addition, an inequality sign "<" is shown between the two numbers.

Answer button group 42 includes four buttons 42a to 42d operatable by subject 2. Four buttons 42a to 42d are answer options to questions 41. In the example shown in FIG. 5, four buttons 42a to 42d are arranged in two rows and two columns. Each row displays header information of "correct" and "incorrect" to cause the subject to choose whether the inequality sign between the two numbers is "correct" or "incorrect." Each column displays header information of "the same" or "different" to cause the subject to choose whether the two terms belong to "the same" or "different" meaning categories.

For example, with respect to questions 41 shown in FIG. 5, "dog" and "spoon" belong to different categories and the inequality sign is incorrect. The correct answer is thus button 42d. What is displayed on question screen 40 is not limited to the example shown in FIG. 5.

While display unit 11 of operation terminal 10 displays the questions in this embodiment, the configuration is not limited thereto. Operation terminal 10 may include a sound output unit, such as a speaker, that announces and presents the questions to subject 2. Similarly, operation terminal 10 may include a sound collector, such as a microphone, that obtains the voice of subject 2 answering the questions. Accordingly, a person who is visually disabled or whose hands are disabled may also serve as subject 2, that is, the depth of concentration of various people can be evaluated.

Data Collection Device

Data collection device 20 obtains the answer time required by subject 2 to answer the questions. As shown in FIG. 4, data collection device 20 includes storage unit 21, presentation control unit 22, and time measurement unit 23.

Storage unit 21 is a memory for storing question information 24 and answer result information 25. Storage unit 21 is, for example, a non-volatile memory such a hard disk drive (HDD) or a flash memory.

Question information 24 indicates the plurality of questions and the correct answers in association with each other.

Answer result information 25 indicates the times required to answer the questions. Answer result information 25 may indicate the answer times in association with the correctness of the answers to the questions. Since the questions are at the same difficulty level, answer result information 25 may indicate only the answer times without the questions and the answer time being associated with each other.

Presentation control unit 22 performs control for presenting the plurality of questions to subject 2. Specifically, presentation control unit 22 reads out question information 24 from storage unit 21, and generates question screen 40 based on read-out question information 24. Presentation control unit 22 causes display unit 11 of operation terminal 10 to display generated question screen 40.

Presentation control unit 22 causes display unit 11 to display a set of the plurality of questions one by one upon receipt of the answers of the previous questions. While each set may include 100 to 1000 questions, the number of the included questions is not particularly limited.

Time measurement unit 23 is, for example, a timer that measures times required to answer the respective questions. Specifically, time measurement unit 23 receives, from input unit 12 of operation terminal 10, the answer information indicating the button selected by subject 2. Time measurement unit 23 measures, as an answer time, the period from when presentation control unit 22 sends question screen 40 to when time measurement unit 23 receives the answer information. At this time, time measurement unit 23 may correct the time required for communications between operation terminal 10 and data collection device 20.

Operation terminal 10 may include time measurement unit 23. For example, time measurement unit 23 included in operation terminal 10 may measure, as an answer time, the time from when display unit 11 displays question screen 40 to when the subject pushes one of four buttons 42a to 42d indicating answer options. There is then no need to consider the influence of the time required for the communications between operation terminal 10 and data collection device 20, which improves the accuracy in measuring the answer time.

Intellectual Productivity Evaluation Device

Intellectual productivity evaluation device 30 evaluates the intellectual productivity of subject 2. Specifically, intellectual productivity evaluation device 30 evaluates the depth of concentration of subject 2 doing intellectual work. As shown in FIG. 4, intellectual productivity evaluation device 30 includes obtainment unit 31, evaluation unit 32, and output unit 33.

Obtainment unit 31 obtains the set of answer times, that is, answer time data. The answer times are the times required by subject 2 to accomplish a task of answering the plurality of questions that is imposed on the subject as intellectual work. That is, obtainment unit 31 obtains the answer times for the respective questions. In this embodiment, obtainment unit 31 obtains answer result information 25 stored in storage unit 21 of data collection device 20.

Evaluation unit 32 calculates an evaluation value related to the depth of concentration of subject 2 in the concentrated state using the set of answer times obtained by obtainment unit 31 based on the concentration model shown in FIG. 3. Specifically, evaluation unit 32 calculates, as the evaluation value, the ratio of time $T_1$ of first deepest concentration in which subject 2 is most deeply concentrated to time T' when subject 2 is concentrated.

As described above, in this embodiment, the concentrated state includes only two of the first deepest concentration and the second deepest concentration. The time T' of concentration is thus the sum of time $T_1$ of first deepest concentration and time $T_2$ of second deepest concentration in which subject 2 is second most deeply concentrated.

Here, the evaluation value calculated by evaluation unit 32 is regarded as a concentration depth index (CDI). The CDI is an index indicating the depth of concentration and expressed by the following Equation 1.

[Math. 1]

$$CDI = \frac{T_1}{T'} = \frac{T_1}{T_1 + T_2} \qquad \text{Equation 1}$$

The CDI expressed by Equation 1 is a value indicating the ratio of the first deepest concentration to the time of concentration. A greater CDI means a higher ratio of the deeply concentrated state. That is, it is found that under the environment with a greater CDI, subject 2 is more deeply concentrated, the work efficiency improves more, and the work time decreases more.

The evaluation value calculated by evaluation unit 32 may not be limited to the CDI. Evaluation unit 32 may calculate, as an alternative evaluation value, a multi-concentration time ratio (MCTR). An MCTR is indicated by time T' to the time required to answer all the plurality of questions, that is, total answer time T. Total answer time T is the time when subject 2 does intellectual work, and corresponds to the total measurement time, that is, the work time. The MCTR is expressed by the following Equation 2.

[Math. 2]

$$MCTR = \frac{T'}{T} = \frac{T_1 + T_2}{T} \qquad \text{Equation 2}$$

The MCTR expressed by Equation 2 indicates the ratio of the sum of the times for transitions between the first deepest concentration and the second deepest concentration to the total work time. A greater MCTR means a higher ratio of the time of concentration. That is, it is found that under the environment with a greater MCTR, subject 2 is concentrated longer, the work efficiency improves more, and the work time decreases more.

While the details will be described later, the depth of concentration is analyzed to calculate the MCTR. That is, including the evaluation on the depth of concentration, MCTRs can represent the ratios of various states of subject 2 to the time of concentration.

Even if the concentrated state also includes the third deepest or shallower concentration, the CDI and the MCTR can be expressed by the Equation 1 and Equation 2 described above. Alternatively, evaluation unit 32 may calculate, as a further evaluation value, the value obtained where the denominator of Equation 1 and the numerator of Equation 2 is $T_1+T_2+T_3\ldots$.

In this embodiment, evaluation unit 32 includes distribution generation unit 34, fitting unit 35, and calculation unit 36, as shown in FIG. 4.

Distribution generation unit 34 generates, using the set of answer times, an answer time distribution indicating the number of answers obtained in the respective answer times. The answer time distribution is represented by the answer time histogram, for example, as shown in FIG. 6, in which the answer time is divided into a plurality of slots and the number of answers included in each slot is regarded as an answer frequency.

Figure 6:
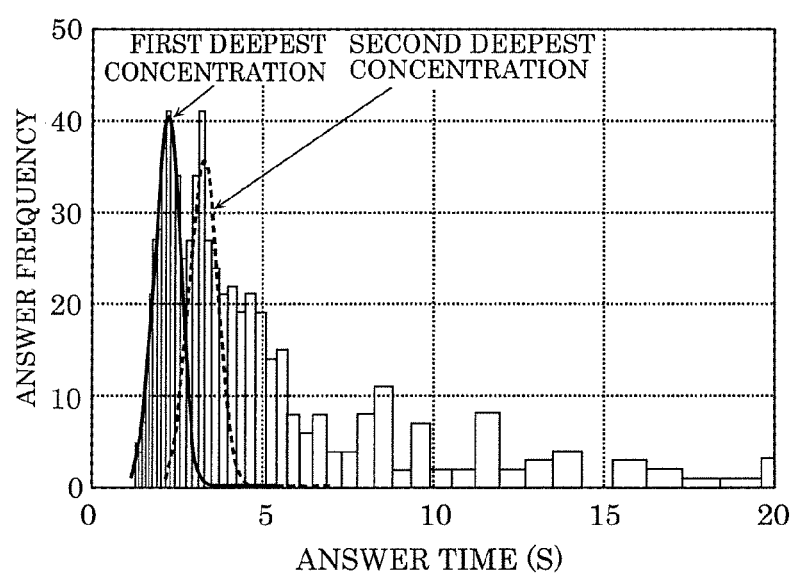
FIG. 6 illustrates an answer time histogram and log-normal distributions associated with the first deepest concentration and the second deepest concentration.

FIG. 6 illustrates an answer time histogram and lognormal distributions associated with the first deepest concentration and the second deepest concentration. In FIG. 6, the horizontal axis represents the logarithm of an answer time, whereas the vertical axis represents an answer frequency.

In the answer time histogram shown in FIG. 6, the answer time is divided into the plurality of slots and the number of answers included in each slot is regarded as the answer frequency. The answer time histogram shown in FIG. 6 is an example of the answer time distribution generated by distribution generation unit 34.

The more subject 2 is concentrated, the shorter the answer time is. The answer for about 1.5 seconds to about 3 seconds corresponds to the first deepest concentration, whereas the answer for about 3 seconds to about 5 seconds corresponds to the second deepest concentration. The answer requiring a time longer than 5 seconds is the answer in the third deepest or shallower concentration or the unconcentrated state.

As shown in FIG. 6, two peaks are found in a shorter answer time. In the concentration model according to this embodiment, the transition probabilities establish a certain Markov model. The first of the two peaks with a shorter answer time is approximated by the log-normal distribution of the first deepest concentration. On the other hand, the second of the two peaks with a longer answer time is approximated by the log-normal distribution of the second deepest concentration.

In this embodiment, distribution generation unit 34 generates, as an answer time distribution, the cumulative distribution of the answer times. Specifically, distribution generation unit 34 sorts the set of answer times in ascending order of the answer times and smoothens the answer times to generate, as the answer time distribution, a distribution represented by the number of cumulative answers in the answer time. This reduces degradation in the approximation accuracy caused by the width of slots in the histogram. The details will be described later.

Fitting unit 35 fits curve $F_1$ of first deepest concentration and curve $F_2$ of second deepest concentration to the answer time distribution. Curve $F_1$ is the distribution function of the log-normal distribution associated with the first deepest concentration, whereas $F_2$ is the distribution function of the log-normal distribution associated with the second deepest concentration. Specifically, fitting unit 35 fits curve $F_1$ of first deepest concentration to a first subset of the answer times shorter than first threshold Th1, in the answer time distribution. Fitting unit 35 fits curve $F_2$ of second deepest concentration to a second subset of the answer times shorter than second threshold Th2, in the answer time distribution other than the first subset.

Here, curve $F_1$ of first deepest concentration is the cumulative distribution function of the log-normal distribution associated with the first deepest concentration. Curve $F_2$ of second deepest concentration is the cumulative distribution function of the log-normal distribution associated with the second deepest concentration. The cumulative distribution function is defined by the following Equations 3 and 4 using three parameters ($\mu$, $\sigma$, p).

[Math. 3]

$$F(t) = \frac{p}{2} \text{erfc}\left(-\frac{\ln(t) - \mu}{\sqrt{2}\,\sigma}\right) \quad \text{Equation 3}$$

$$\text{erfc}(x) = \frac{2}{\sqrt{\pi}} \int_x^\infty e^{-s^2} ds \quad \text{Equation 4}$$

Curve $F_1$ of first deepest concentration can be expressed using parameters ($\mu_1$, $\sigma_1$, $p_1$), whereas curve $F_2$ of second deepest concentration can be expressed using parameters ($\mu_2$, $\sigma_2$, $p_2$).

Figure 7:
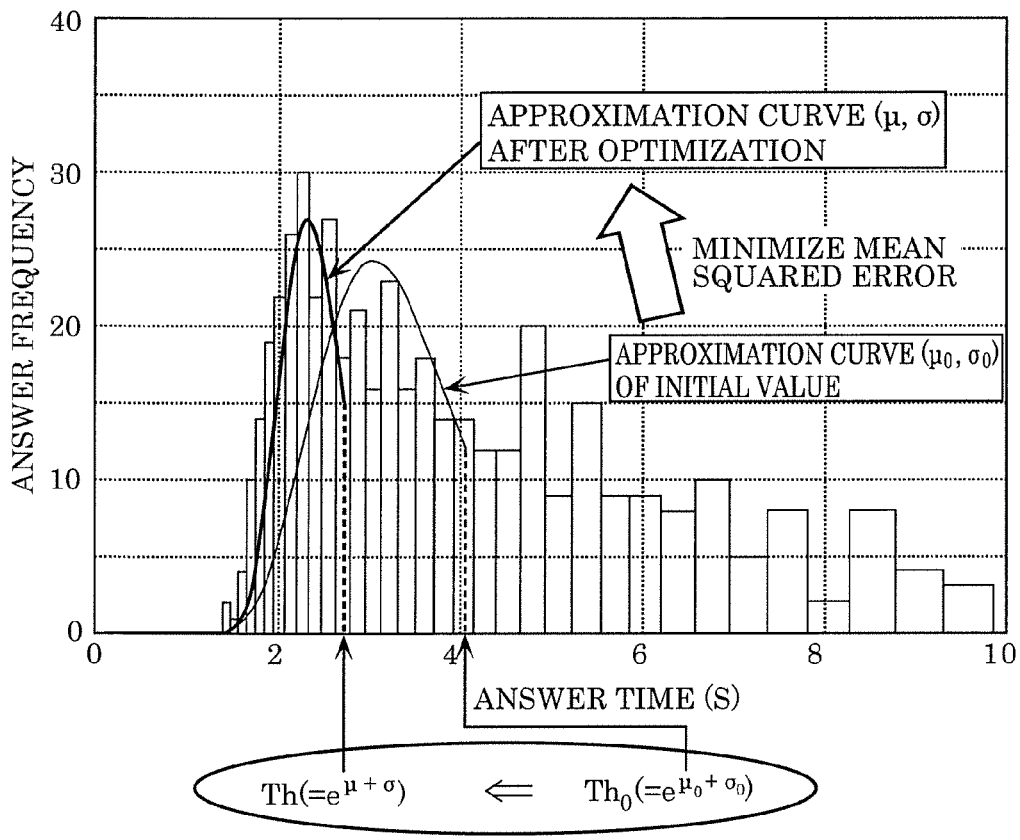
FIG. 7 illustrates an example of an approximation method of the log-normal distributions in the answer time histogram shown in FIG. 6.

FIG. 7 illustrates approximation of a log-normal distribution in the answer time histogram shown in FIG. 6. As shown in FIG. 7, fitting unit 35 approximates the log-normal distribution not for the whole set of answer times but for subsets of answer times shorter than threshold Th. This determines the parameters of approximation curves, that is, concentration curves. The curves of the first deepest concentration and the second deepest concentration are determined in this manner. Threshold Th is a data reduction threshold for reducing data to be approximated. Threshold Th as the data reduction threshold is expressed by the following Equation 5.

[Math. 4]

$$Th = e^{\mu + \sigma} \quad \text{Equation 5}$$

Specifically, fitting unit 35 performs approximation while changing the data reduction threshold. For example, as shown in FIG. 7, first, fitting unit 35 calculates an approximation curve based on initial threshold $Th_0$ and then a mean squared error between the approximation curve and target data. Fitting unit 35 changes the data reduction threshold to minimize the mean squared error, thereby calculating the approximation curve.

In this embodiment, since distribution generation unit 34 generates the cumulative distribution as the answer time distribution, fitting unit 35 approximates the cumulative distribution. The details will be described later.

Calculation unit 36 calculates time $T_1$ of first deepest concentration and time $T_2$ of second deepest concentration based on curve $F_1$ of first deepest concentration and curve $F_2$ of second deepest concentration, respectively. Time $T_1$ of first deepest concentration is the product of number $N_1$ of answers processed in the first deepest concentration and expected value $E_1$ of the answer times. Time $T_2$ of second deepest concentration is the product of number $N_2$ of answers processed in the second deepest concentration and expected value $E_2$ of the answer times.

Detailed processing of distribution generation unit 34, fitting unit 35, and calculation unit 36 will be described later using a set of answer times as an example.

Output unit 33 outputs the evaluation value information indicating the evaluation value calculated by evaluation unit 32. For example, output unit 33 may output the evaluation value information to system 40. The control unit of system 40 determines details how to control system 40 based on the evaluation value information, and controls system 40 based on the determined control details. For example, the control unit of system 40 stores, as association information, the evaluation value and the control details in association with each other, for example, at a memory. The control unit reads out the association information from the memory and refers to the association information to determine how to control the system in association with the evaluation value. For example, if the evaluation value is low, system 40 operates to create the ambient environment capable of improving the evaluation value.

Output unit 33 determines the control details of system 40 based on the evaluation value information, and may output control signals for operating system 40 based on the determined control details. Intellectual productivity evaluation device 30 may be a control device of system 40.

Here, system 40 controls the ambient environment of subject 2. For example, as shown in FIG. 1, system 40 is an air conditioner. System 40 adjusts the temperature or humidity of the space where subject 2 stays. Alternatively, system 40 adjusts, for example, the amount and direction of air blowing subject 2 and the surrounding. The control for improving the evaluation value may include, for example, reduction in the temperature of the space or the air blow against subject 2.

System 40 may be a lighting system that adjusts the brightness of the space where subject 2 stays. System 40 adjusts the amount and color of emitted light. The control for improving the evaluation value may include, for example, improvement in the color temperature of the light for illuminating the space or an increase in the brightness of the space, but are not limited thereto.

System 40 may be a speaker that outputs music, for example. The speaker may have a noise canceling function. The control for improving the evaluation value may include, for example, execution of noise canceling to allow subject 2 to hear little noise.

System 40 may be, for example, an aroma diffuser that emits fragrant substances to the space where subject 2 stays. Alternatively, system 40 may be a system that emits ion substrates such as nanoe (trademark). The control for improving the evaluation value may include, for example, emission of fragrant substances, such as mint, exhibiting cool stimulation, but are not limited thereto.

System 40 may adjust the degree (or index) of air quality in the space where subject 2 stays. The air quality depends on, for example, carbon dioxide or dust. Alternatively, system 40 may adjust the amount of particle substances in the space where subject 2 stays. The particle substances may be, for example, PM2.5 or PM10. Specifically, system 40 may be an air cleaner or a ventilator. The control for improving the evaluation value may include, for example, reduction in the carbon dioxide concentration or PM2.5 by ventilation, but are not limited thereto.

Output unit 33 may be, for example, a display that shows the CDI or MCTR as an example of the evaluation value. At this time, output unit 33 may also display the answer time distribution generated by distribution generation unit 34. Alternatively, output unit 33 may be a speaker that outputs the CDI or the MCTR as sound.

Output unit 33 may communicate with operation terminal 10. For example, output unit 33 sends the CDI or the MCTR to operation terminal 10 to cause display unit 11 of operation terminal 10 to display the CDI or the MCTR.

For example, output unit 33 may output not only the final evaluation value such as the CDI and/or the MCTR, but also, as a comma-separated value (CSV) file, a list of parameters ($\mu$, $\sigma$, p) generated during the calculation of the evaluation value and intermediate indexes (specifically, e.g., $T_1$, $T_2$, $E_1$, and $E_2$). Alternatively, output unit 33 may output, as graphic data, the histogram generated by distribution generation unit 34. The output file format is not limited thereto.

Operation (Intellectual Productivity Evaluation Method)

Now, an operation of intellectual productivity evaluation system 1 according to this embodiment, that is, an intellectual productivity evaluation method will be described using a specific example. The intellectual productivity evaluation method according to this embodiment includes a first step and a second step. The first step is obtainment of answer time data by causing subject 2 to do an intellectual work. The second step is calculation of an evaluation value related to the depth of concentration of subject 2 using the obtained answer time data.

Subject 2 is sufficiently skilled to do answer work. Specifically, subject 2 is sufficiently used to operating operation terminal 10 and the display format of questions and the answer style to do answer work for measuring the intellectual productivity.

Obtainment of Answer Time Data

Figure 8:
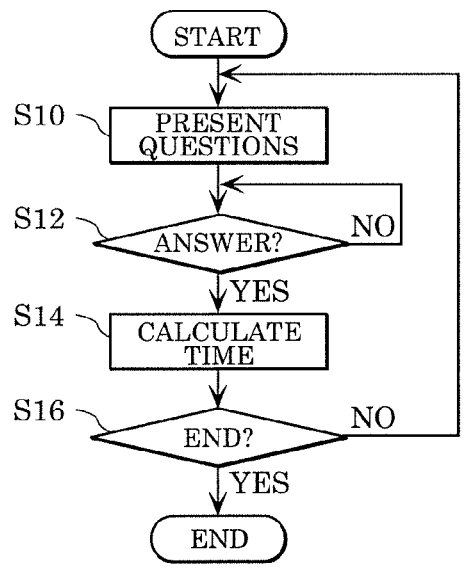
FIG. 8 is a flow chart illustrating how to obtain answer time data in the intellectual productivity evaluation system according to the embodiment.

First, the first step of obtaining a set of answer times will be described with reference to FIG. 8. FIG. 8 is a flow chart illustrating how to obtain answer time data in intellectual productivity evaluation system 1 according to this embodiment.

First, operation terminal 10 presents questions to subject 2 (S10). Specifically, presentation control unit 22 of data collection device 20 reads out question information 24 from storage unit 21, generates question screen 40 including a single set of questions 41, and sends generated question screen 40 to operation terminal 10. Operation terminal 10 receives question screen 40 sent from presentation control unit 22, and display unit 11 displays question screen 40.

After presenting the questions, operation terminal 10 stands by until input unit 12 receives an input of answer from subject 2 (No in S12). If input unit 12 receives the input of answer from subject 2 (Yes in S12), that is, any one of buttons 42a to 42d is selected, time measurement unit 23 calculates the answer time (S14). Specifically, input unit 12 sends answer information indicating the selected button to time measurement unit 23. After presentation control unit 22 has sent question screen 40, time measurement unit 23 calculates, as the answer time for the question, the time until time measurement unit 23 receives the answer information. The calculated answer time is, as answer result information 25, stored in storage unit 21.

At this time, if the received answer is incorrect, presentation control unit 22 may cause display unit 11 of operation terminal 10 to display that the answer is incorrect, thereby prompting subject 2 to input the answer again. Time measurement unit 23 may calculate, as answer time, the time from when presentation control unit 22 has sent question screen 40 to when time measurement unit 23 receives a correct answer. Time measurement unit 23 may correct the time required for communications in the calculation of the answer time.

Until subject 2 completes the answer work to the plurality of questions (No in S16), the process returns to step S10 and repeats the presentation of the questions. Specifically, until the completion of the presentation of a single predetermined set of questions and reception of answers to the questions, the presentation of the questions and answer to the questions are repeated. Alternatively, the presentation of the questions and answer to the questions may be repeated for a predetermined time after the start of the answer work. Note that the answer work to the plurality of questions may end upon receipt of an instruction from subject 2.

Calculation of Evaluation Value

Figure 9:
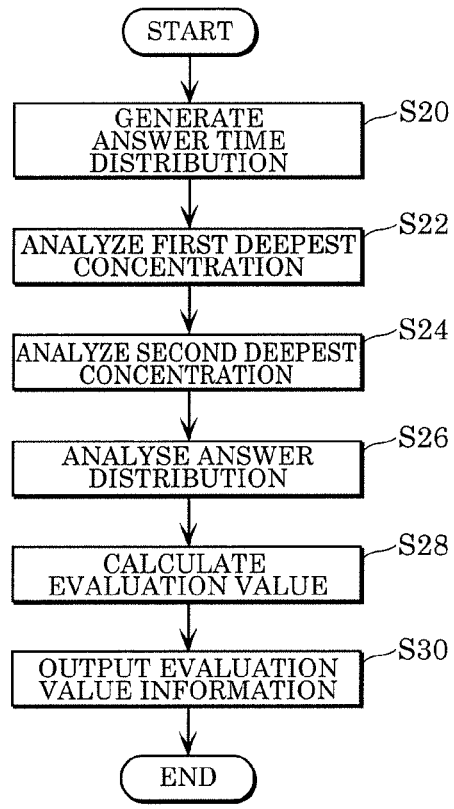
FIG. 9 is a flow chart illustrating how to calculate an evaluation value based on the answer time data in the intellectual productivity evaluation system according to the embodiment.

Next, the second step of calculating an evaluation value related to the depth of concentration of subject 2, specifically, a CDI, using the answer time data will be described with reference to FIG. 9. FIG. 9 is a flow chart illustrating how to calculate an evaluation value based on the answer time data in intellectual productivity evaluation system 1 according to this embodiment.

First, distribution generation unit 34 generates an answer time distribution (S20). In this embodiment, distribution generation unit 34 generates, using a set of answer times, the cumulative distribution of answer times as the answer time distribution. Specifically, as shown in FIG. 10, distribution generation unit 34 sorts the answer times in ascending order, and then smoothens the answer times by a five-point moving average to generate the cumulative distribution of the answer times.

Figure 10:
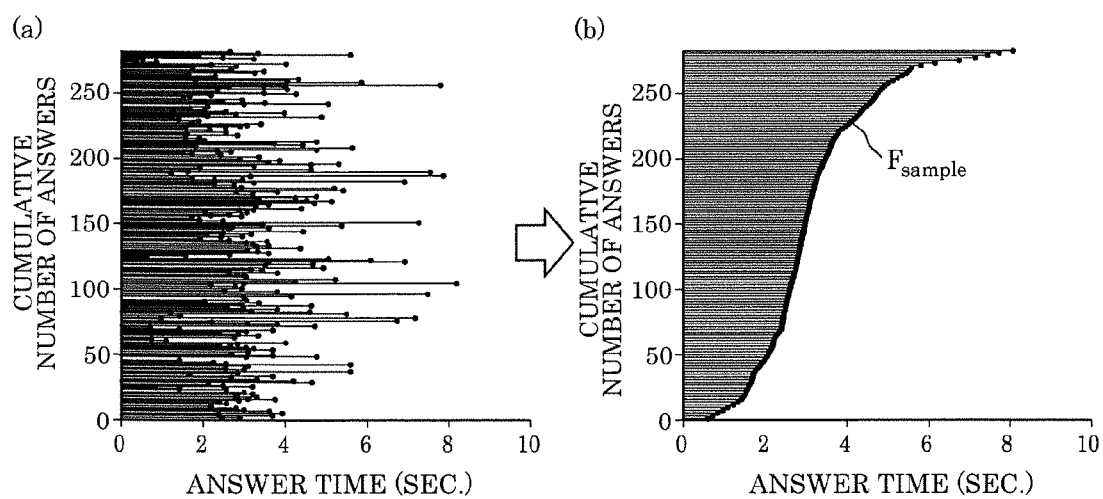
FIG. 10 illustrates sorting of answer time data.

Now, FIG. 10 illustrates sorting of answer time data, namely, (a) illustrates the answer time data before sorting, and (b) illustrates answer time data $F_{sample}$ after the sorting. In each of (a) and (b) of FIG. 10, the horizontal axis represents an answer time, whereas the vertical axis represents the number of cumulative answers.

The number of points of the moving average is not limited to five but may be three or ten, for example. The smoothing means is not limited to the moving average.

Next, fitting unit 35 fits curve $F_1$ of first deepest concentration to analyze the first deepest concentration (S22). In this embodiment, the cumulative distribution of the answer times shown in (b) of FIG. 10 is approximated. The approximation may be performed by, for example, a method of steepest descent. The mean squared error between the approximation target and the cumulative distribution function is set as an objective function, and three parameters ($\mu$, $\sigma$, p) of the cumulative distribution function are optimized to minimize the objective function.

Figure 11:
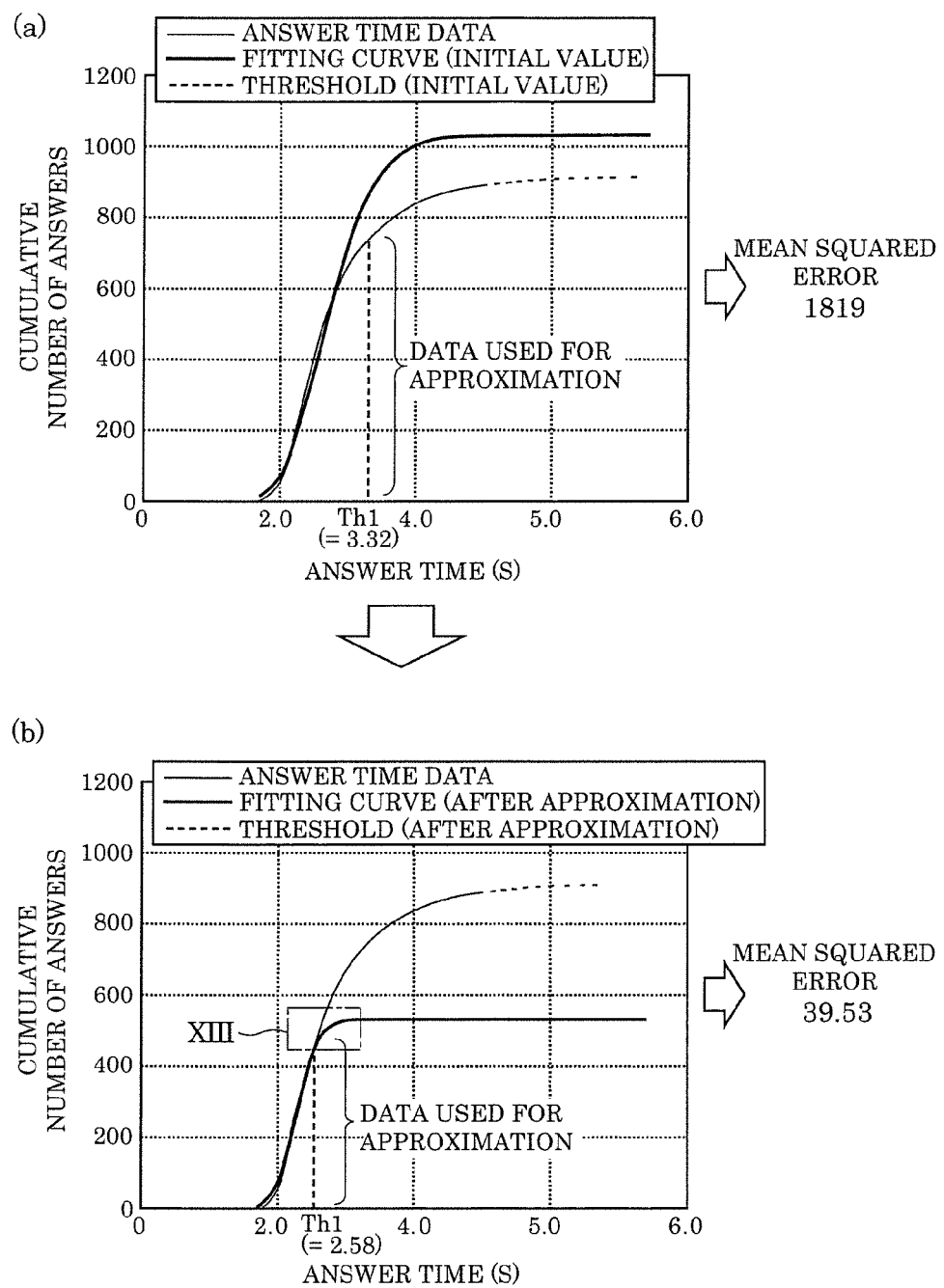
FIG. 11 illustrates approximation of a cumulative distribution function to sorted answer time data.

Specifically, as shown in FIG. 11, fitting unit 35 fits curve $F_1$ of first deepest concentration of the log-normal distribution to, out of the answer time data, the answer times shorter than first threshold Th1 based on Equations 3 to 5. Accordingly, the parameters ($\mu_1$, $\sigma_1$, $p_1$) of curve $F_1$ of first deepest concentration are determined.

FIG. 11 illustrates approximation of the cumulative distribution function to sorted answer time data. In FIG. 11, (a) shows curve $F_1$ of first deepest concentration of the initial value, whereas (b) shows curve $F_1$ of first deepest concentration of after optimization.

Figure 12:
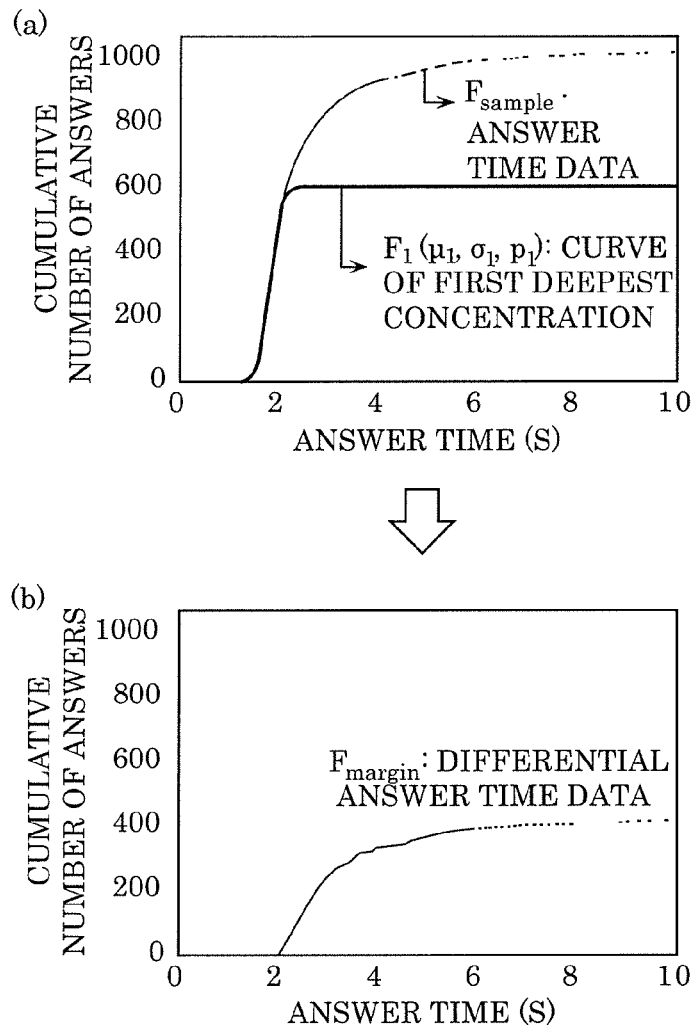
FIG. 12 illustrates how to exclude, from the answer time data, a subset of answer times associated with the first deepest concentration.

Next, fitting unit 35 fits curve $F_2$ of second deepest concentration to analyze the second deepest concentration (S24). Specifically, first, as shown in FIG. 12, the subset of answer times in the first deepest concentration is excluded from answer time data $F_{sample}$ to generate differential answer time data $F_{margin}$. Note that FIG. 12 illustrates how to exclude the subset of answer times associated with the first deepest concentration from answer time data $F_{sample}$.

For example, distribution generation unit 34 subtracts the values corresponding to curve $F_1$ of first deepest concentration from the points of answer time data $F_{sample}$ to generate differential data. Distribution generation unit 34 sorts the differential data in ascending order and smoothens the data to generate differential answer time data $F_{margin}$. Excluding the subset of answer times associated with the first deepest concentration, differential answer time data $F_{margin}$ corresponds to the data representing the second deepest concentration as the first deepest concentration. Fitting unit 35 determines the parameters ($\mu_2$, $\sigma_2$, $p_2$) and curve $F_2$ of second deepest concentration based on the same method as in the first deepest concentration.

Figure 13:
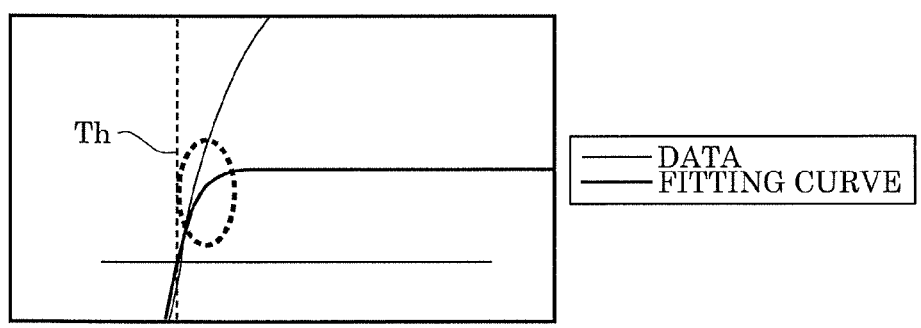
FIG. 13 illustrates questions where a subject is in a mixed state between the first deepest concentration and the second deepest concentration.

Parameter $p_1$ of curve $F_1$ of first deepest concentration and parameter $p_2$ of curve $F_2$ of second deepest concentration correspond to the number of answers processed in the first deepest concentration and the number of answers processed in the second deepest concentration, respectively. However, as indicated by the region circled by a bold broken line in FIG. 13, curve $F_1$ of first deepest concentration also includes a part that is not necessarily approximated. This is because numbers $p_1$ and $p_2$ of answers directly calculated from curve $F_1$ of first deepest concentration and curve $F_2$ of second deepest concentration, respectively, could deviate from the actual answer. Note that FIG. 13 illustrates questions given to the subject in a mixed state of the first deepest concentration and the second deepest concentration. FIG. 13 is an enlarged view of region XIII shown in (b) of FIG. 11.

Evaluation unit 32 analyses a distribution of the answers (S26). Specifically, evaluation unit 32 compares the parameters ($\mu_1$, $\sigma_1$, $p_1$) of curve $F_1$ of first deepest concentration obtained in step S22 and the parameters ($\mu_2$, $\sigma_2$, $p_2$) of curve $F_2$ of second deepest concentration obtained in step S24 with actual answer time data $F_{sample}$ again. This is to calculate number $N_1$ of answers processed in the first deepest concentration and number $N_2$ of answers processed in the second deepest concentration.

More specifically, first, assume that P is the sum of answers processed in the first deepest concentration and the second deepest concentration. P is the sum of $p_1$ of curve $F_1$ of first deepest concentration and $p_2$ of curve $F_2$ of second deepest concentration, that is $P=p_1+p_2$.

Fitting unit 35 fits composite concentration curve $F_{sum}$ of curve $F_1$ of first deepest concentration and curve $F_2$ of second deepest concentration (i.e., $F_{sum}=F_1(\mu_1, \sigma_1, N_1)+F_2(\mu_2, \sigma_2, N_2)$) to a subset of answer times shorter than second threshold Th2 in the answer time distribution. Specifically, fitting unit 35 calculates error $\varepsilon$ ($N_1$, $N_2$) of mean square between composite concentration curve $F_{sum}$ and the answer time data for the subset of answer times shorter than second threshold Th2. At this time, numbers $N_1$ and $N_2$ of answers satisfy relations $N_1+N_2=[P]$, $N_1 \geq 0$, and $N_2 \geq 0$, where [ ] is a Gauss symbol. Second threshold Th2 is obtained by assigning parameters $\mu_2$ and $\sigma_2$ of curve $F_2$ of second deepest concentration to Equation 5.

Figure 14:
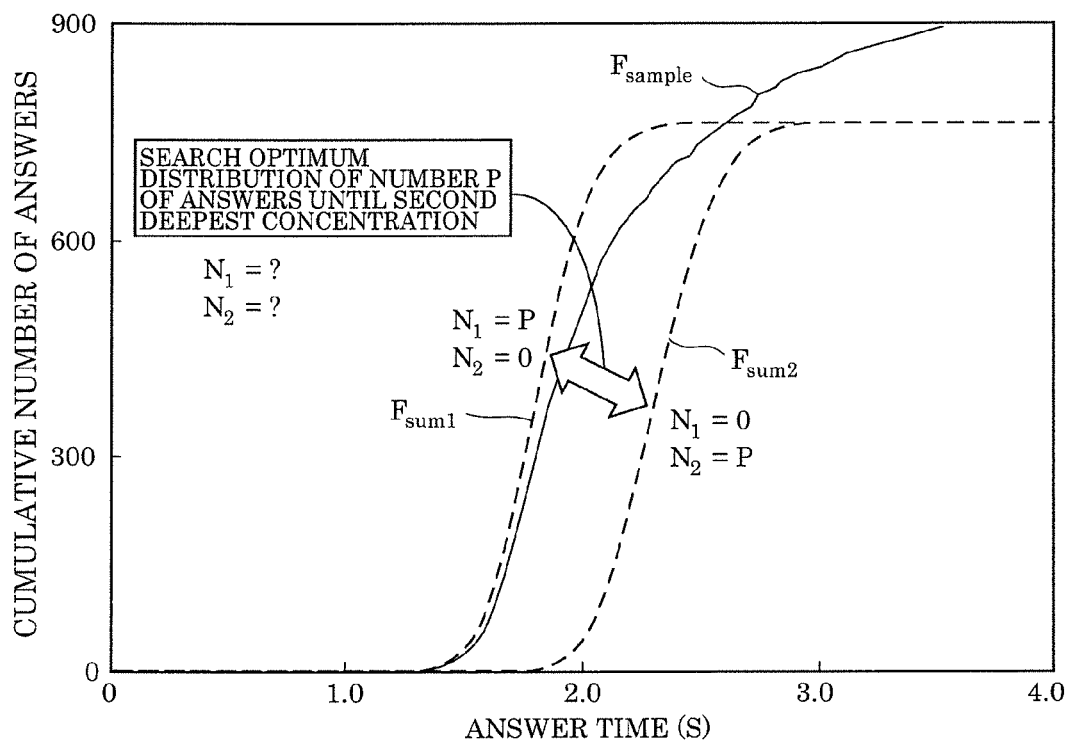
FIG. 14 illustrates how to determine the numbers of answers processed in the first deepest concentration and the second deepest concentration.

FIG. 14 illustrates how to determine the number of processed questions in the first deepest concentration and the second deepest concentration. In FIG. 14, the solid line represents answer time data $F_{sample}$, whereas the broken lines represent two composite concentration curves $F_{sum1}$ and $F_{sum2}$.

Composite concentration curve $F_{sum1}$ is composite concentration curve $F_{sum}$ on assumption that all the "answers processed in the first deepest concentration and the second deepest concentration" are processed in the first deepest concentration, that is, $N_1=P$. On the other hand, composite concentration curve $F_{sum2}$ is composite concentration curve $F_{sum}$ on assumption that all the "answers processed in the first deepest concentration and the second deepest concentration" are processed in the second deepest concentration, that is, $N_2=P$. Fitting unit 35 determines an optimum composite concentration curve $F_{sum}$ between $F_{sum1}$ and $F_{sum2}$.

Figure 15:
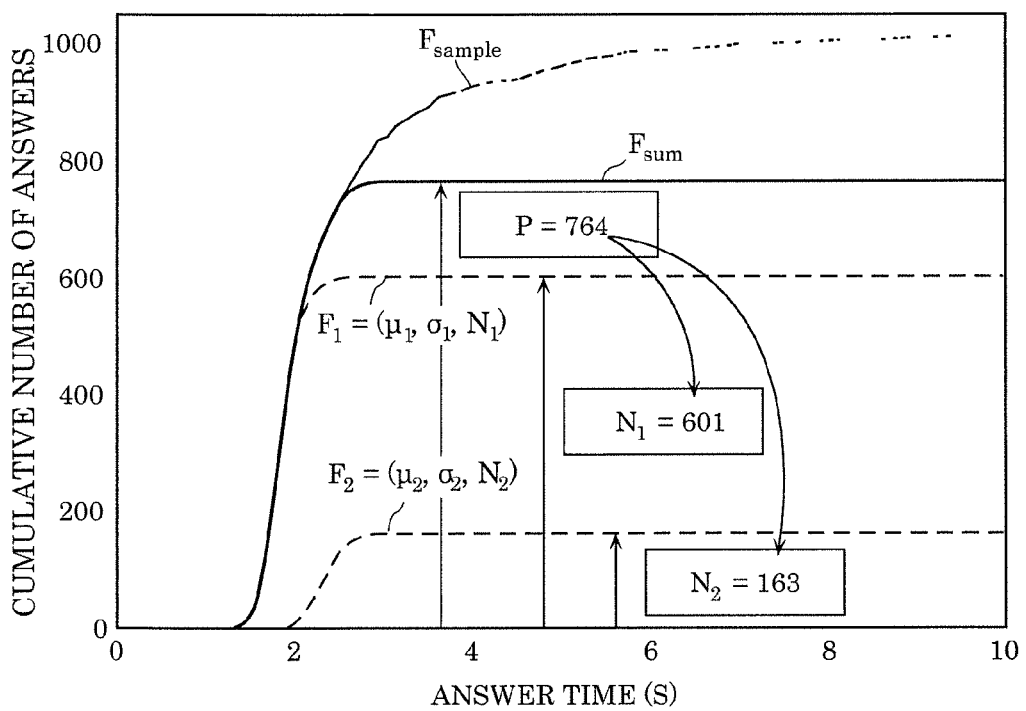
FIG. 15 illustrates an example where the numbers of answers processed in the first deepest concentration and the second deepest concentration are optimized.

Specifically, fitting unit 35 determines a curve minimizing error $\varepsilon$ ($N_1$, $N_2$) of mean square and calculates the values of $N_1$ and $N_2$ at this time. FIG. 15 illustrates an example where the numbers of questions processed in the first deepest concentration and the second deepest concentration are optimized. As shown in FIG. 15, parameter $p_1$ of curve $F_1$ of first deepest concentration and parameter $p_2$ of curve $F_2$ of second deepest concentration are replaced with $N_1$ and $N_2$, respectively, by adjusting the number of answers.

Next, calculation unit 36 calculates an evaluation value related to the depth of concentration (S28). Specifically, calculation unit 36 first calculates expected value $E_1$ of the answer times and time $T_1$ of first deepest concentration as well as expected value $E_2$ of the answer times and time $T_2$ of second deepest concentration based on the following Equations 6 and 7.

[Math. 5]

$$E_k = e^{\mu_k + \frac{\sigma_k^2}{2}} \quad (k = 1, 2) \quad \text{Equation 6}$$

$$T_l = E_l \times N_l \quad (l = 1, 2) \quad \text{Equation 7}$$

Accordingly, since time $T_1$ of first deepest concentration and time $T_2$ of second deepest concentration are calculated to cause calculation unit 36 to calculate the evaluation value, such as such as the CDI or the MCTR, related to the depth of concentration based on Equation 1 or 2. The calculated evaluation value is then output by output unit 33 (S30).

Advantages

As described above, intellectual productivity evaluation device 30 according to this embodiment includes obtainment unit 31, evaluation unit 32, and output unit 33. Obtainment unit 31 obtains a set of answer times required by subject 2 to accomplish a task of answering a plurality of questions that is imposed on the subject as intellectual work. Evaluation unit 32 calculates an evaluation value related to the depth of concentration of subject 2 in the concentrated state using the set of answer times obtained by obtainment unit 31. The calculation is based on the model in which subject 2 is in the concentrated state or the unconcentrated state when doing intellectual work. Output unit 33 outputs the evaluation value information indicating the evaluation value calculated by evaluation unit 32.

This configuration causes intellectual productivity evaluation device 30 to support an improvement in the efficiency of the operation of system 40.

Specifically, intellectual productivity evaluation device 30 calculates the evaluation value related to the depth of concentration in the concentrated state. This leads to objective and quantitative evaluation of the quality of concentration, which causes intellectual productivity evaluation device 30 to improve office environment, for example. Specifically, intellectual productivity evaluation device 30 calculates evaluation values of the intellectual productivity under a plurality of environmental conditions, thereby objectively and quantitatively evaluating, under which environment the objective can be deeply concentrated.

System 40 is then operated to create the environment that is evaluated by intellectual productivity evaluation device 30 as the environment under which the objective can be deeply concentrated. This improves the work efficiency and reduces the work time. This causes workers or officers to leave the workplace on time or earlier and reduces the time of operating lighting systems and air conditioners, which leads to a decrease in energy consumption. In this manner, intellectual productivity evaluation device 30 according to this embodiment controls system 40 based on the evaluation value information to support effective operation of system 40. Accordingly, the device supports an improvement in the efficiency of, for example, service work at offices and work in the other industry such as manufacturing.

The plurality of environments may depend on, for example, whether or not a worker is motivated or may be created by adjusting heat. The heat is adjustable by operation conditions of, for example, an air conditioner.

For example, the concentrated state includes the first deepest concentration which is a mixture of the working state and the briefly interrupted state, and the second deepest concentration that is also a mixture of the working state and the briefly interrupted state. The subject is less deeply concentrated in the second deepest concentration than in the first deepest concentration. Evaluation unit 32 calculates, as an evaluation value, the ratio of time $T_1$ of first deepest concentration in which subject 2 is most deeply concentrated to the time of concentration in which subject 2 is concentrated.

This configuration distinguishes whether the subject is deeply or shallowly concentrated at a time of concentration.

Figure 16A:
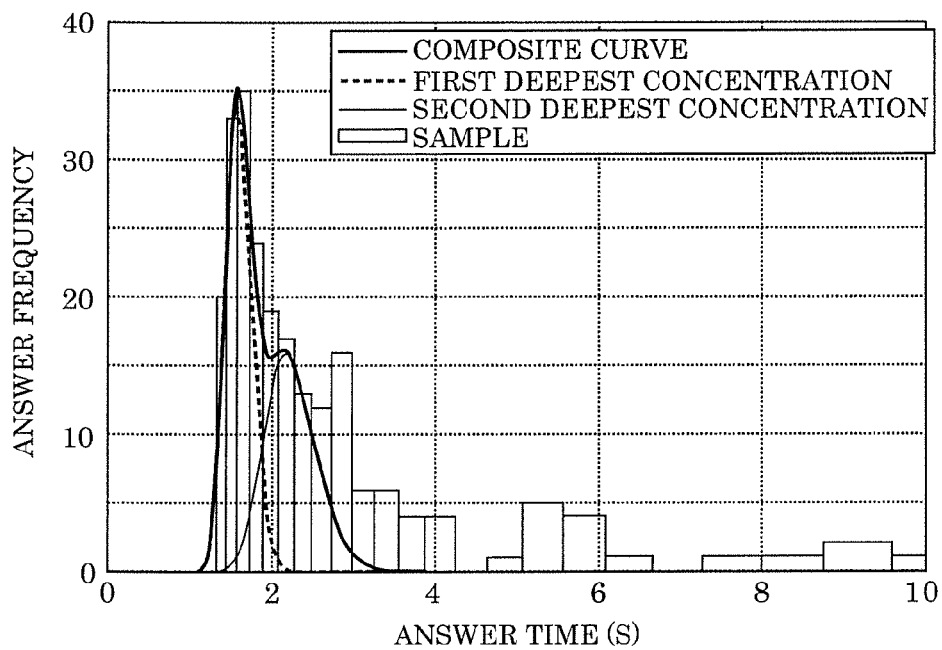
FIG. 16A illustrates an example of a histogram in which the first deepest concentration is dominant.
Figure 16B:
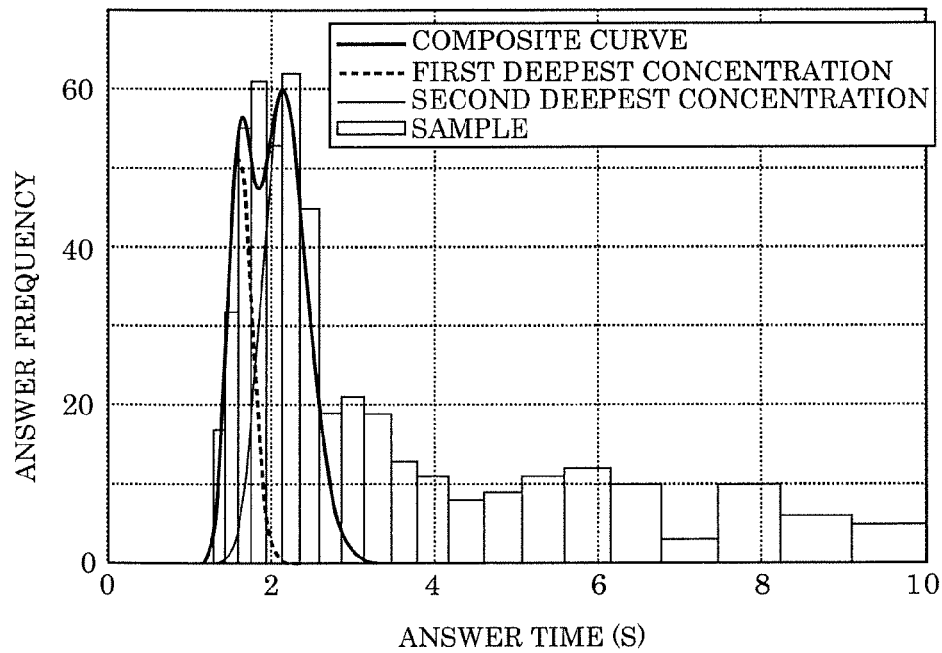
FIG. 16B illustrates an example of a histogram in which the second deepest concentration is dominant.

For example, FIGS. 16A and 16B illustrate an example of an answer time histogram where the depths of concentration are different at the same time of concentration. FIG. 16A illustrates an example of a histogram where the first deepest concentration is dominant, that is, the CDI is greater than 50%. FIG. 16B illustrates an example of a histogram where the second deepest concentration is dominant, that is, the CDI is smaller than 50%.

As clear from the comparison between FIGS. 16A and 16B, the greater the CDI is, the larger number of answers are obtained in a short time and the more deeply the subject is concentrated on the work. That is, the evaluation of the depth of concentration causes the experimenter to figure out the work speed and the level of work. For example, time T' is the sum of time $T_1$ of first deepest concentration and time $T_2$ of second deepest concentration in which subject 2 is second most deeply concentrated.

With this configuration, the concentrated state is divided into the two stages of the first deepest concentration and the second deepest concentration in most cases. This reduces the amount of processing required to calculate the evaluation value, while allowing highly reliable calculation of the evaluation value. An increase in the reliability of the evaluation value increases the reliably in the evaluation on the environment. This allows support of efficient operation of system 40 to create the environment suitable for the characteristics such as deep concentration or long concentration. Accordingly, improvement in the work efficiencies under the respective environments are expected, which further contributes to reduction in the energy consumption due to reduction in the work time or other factors.

This method is applicable to evaluation on not only the environment but also on the effect of medicines such as eye drops or supplements. Specifically, the experimenter may cause subject 2 to take supplements to evaluate the depth of concentration of the subject after taking the supplements. This allows evaluation of the effect of the supplements on the depth of concentration.

This method is applicable not only to the evaluation on the effect of the medicines or the supplements but also to evaluation on the effect of recovering the power of concentration using, for example, a system that prompts a break. Specifically, the experimenter may cause subject 2 to use the system to evaluate the depth of concentration before and after the use, thereby evaluating the effect of the system recovering the power of concentration. This method is also applicable to designing or improvement of a system having more effect of recovering the power of concentration.

This method is applicable not only to the designing or improvement of a system but also to designing of the space. For example, a plurality of environments are prepared which are different from each other in at least one factor. The factor may include heat conditions such as the temperature and the humidity, optical conditions such as the brightness and the color temperature, and sound conditions. Evaluation on the concentration of subject 2 under these environments allows objective evaluation on the ease of concentration under the respective environments. This achieves designing of the space with a higher evaluation value. The environments may include the colors of the ceiling, walls, or floor and the location(s) of furniture and home appliances.

For example, evaluation unit 32 includes distribution generation unit 34, fitting unit 35, and calculation unit 36. Generation unit 34 generates, using a set of answer times, an answer time distribution indicating the number of answers in each of the answer times. Fitting unit 35 fits curve $F_1$ of first deepest concentration and curve $F_2$ of second deepest concentration to the answer time distribution. Curve $F_1$ is a distribution function of a log-normal distribution associated with the first deepest concentration, whereas curve $F_2$ is a distribution function of a log-normal distribution associated with the second deepest concentration. Calculation unit 36 calculates time $T_1$ of first deepest concentration and time $T_2$ of second deepest concentration based on curve $F_1$ of first deepest concentration and curve $F_2$ of second deepest concentration. Time $T_1$ is the product of number $N_1$ of answers processed in the first deepest concentration and expected value $E_1$ of the answer times. Time $T_2$ is the product of number $N_2$ of answers processed in the second deepest concentration and expected value $E_2$ of the answer times.

This allows representation of the concentration model by the Markov model, and calculation of highly reliable evaluation values by approximation using the log-normal distributions.

For example, fitting unit 35 fits curve $F_1$ of first deepest concentration to a first subset of the answer times shorter than first threshold Th1 in answer time distribution. Fitting unit 35 also fits curve $F_2$ of second deepest concentration to a second subset of the answer times shorter than second threshold Th2 in the answer time distribution other than the first subset.

This limits target data of the log-normal distributions approximated for the respective depths of concentration, thereby improving the accuracy of approximation. An improvement in the accuracy of approximation improves the reliability of the evaluation value.

For example, curve $F_1$ of first deepest concentration is the cumulative distribution function of the log-normal distribution associated with the first deepest concentration. Curve $F_2$ of second deepest concentration is the cumulative distribution function of the log-normal distribution associated with the second deepest concentration. Distribution generation unit 34 sorts a set of answer times in ascending order of the answer times and then smoothen the answer times to generate, as an answer time distribution, the distribution indicated by the number of cumulative answers in the answer times.

Accordingly, the curves are fitted to the cumulative distribution of the answer times. This reduces a decrease in the approximation accuracy due to the widths of slots in the histogram as compared to the case of fitting the curves to the answer time histogram.

For example, the intellectual productivity evaluation method according to this embodiment includes the step of obtaining a set of answer times, and the step of calculating an evaluation value related to the depth of concentration of subject 2 in the concentrated state. The set of answer times is the time required by subject 2 to accomplish a task of answering a plurality of questions that is imposed on the subject as intellectual work. In the step of calculating, the evaluation value is calculated using the obtained set of answer times based on the model in which subject 2 is in the concentrated state or the unconcentrated state during the intellectual work.

This allows calculation of the evaluation value related to the depth of concentration in the concentrated state, and thus objectively and quantitatively evaluation of the quality of concentration.

Variation

While an example has been described in the embodiment where the MCTR or the CDI is used as an example of the evaluation value, the evaluation value may be a concentration time ratio (CTR). The CTR is an index indicating the ratio of the period Tc of the concentrated state to the total answer period T. That is, the CTR is expressed by the following Equation 8.

[Math. 6]

$$CTR = \frac{T_C}{T} \quad \text{Equation 8}$$

Figure 17:
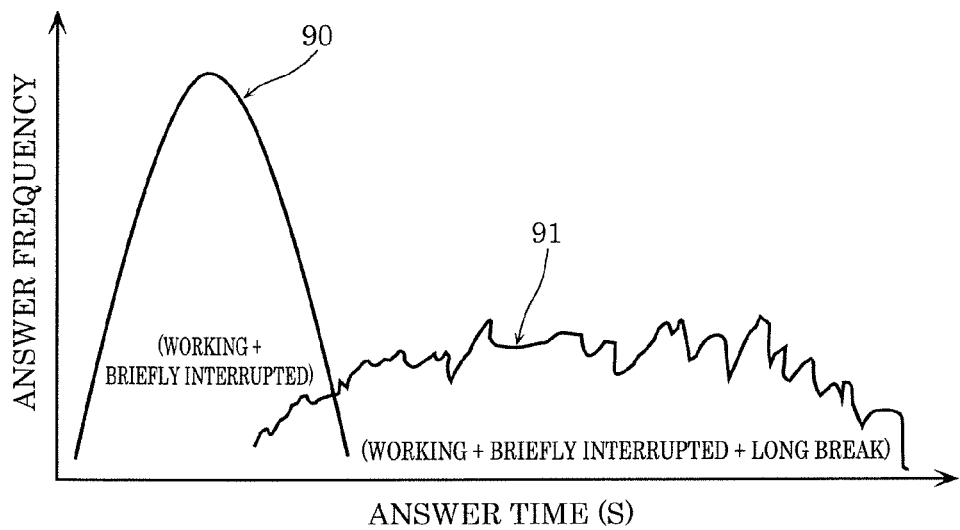
FIG. 17 is an answer time histogram according to a variation of the embodiment and schematically illustrates example distributions in a concentrated state and an unconcentrated state.

FIG. 17 is an answer time histogram according to this variation and schematically illustrates the example distributions in the concentrated state and the unconcentrated state. In the example of FIG. 17, the horizontal axis represents the logarithm of the answer time, whereas the vertical axis represents the answer frequency. The histogram shown in FIG. 17 is, for example, obtained by schematizing the histogram shown in FIG. 6.

As shown in FIG. 17, the histogram can be fitted to the overlap between the two frequency distributions. Specifically, in first frequency distribution 90 with shorter answer times, transitions occur between two states: the "working" state and the "briefly interrupted" state, based on the Markov model with stable transition probabilities. Therefore, first frequency distribution 90 corresponds to the log-normal distribution expressed by Equation 9, for example.

[Math. 7]

$$F(t) = \frac{1}{\sqrt{2\pi}\,\sigma t} \exp\left(-\frac{(\ln(t) - \mu)^2}{2\sigma^2}\right) \quad \text{Equation 9}$$

Note that t is an answer time per question, σ is a standard deviation of a distribution, and μ is an index where the mode of distribution is expressed by $e^\mu$.

On the other hand, in second frequency distribution 91 with longer answer times, random transitions occur among three states: the "working" state, the "briefly interrupted" state, and "long break." This variation focuses not on the depth of concentration. The concentrated state includes two states, the "working" and "briefly interrupted" states, whereas the unconcentrated state corresponds to the "long break."

Period Tc in Equation 8 indicated above is expressed by the following Equation 10.

[Math. 8]

$$T_C = \exp\left(\mu + \frac{\sigma^2}{2}\right) N \quad \text{Equation 10}$$

In Equation 10, N is the total number of answers.

In the answer time histogram, the approximation curve of the log-normal distribution (first frequency distribution 91) can be derived to calculate the CTR using parameters μ and σ of the curve as well as total answer time T and total number N of answers. Since the side of the histogram with longer answer times includes the "long break," a sufficiently reliable CTR can be obtained even with the use of only first frequency distribution 91.

Now, the reliability of the CTR obtained in this variation will be described based on an experiment result. The experiment caused a plurality of subjects 2 to answer a plurality of sets of questions. Subjects 2 did the plurality of sets of answer work in the workspace kept under a constant environment including heat environment such as the temperature and the humidity, optical environment such as the brightness of illumination. The mean value of the answer speed and the CTR were calculated based on the answer time data.

Figure 18A:
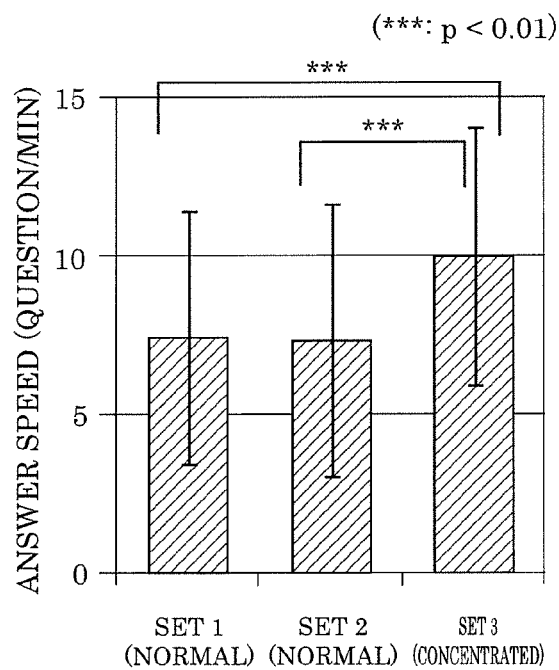
FIG. 18A illustrates a relationship between the working state of a subject and an answer speed.
Figure 18B:
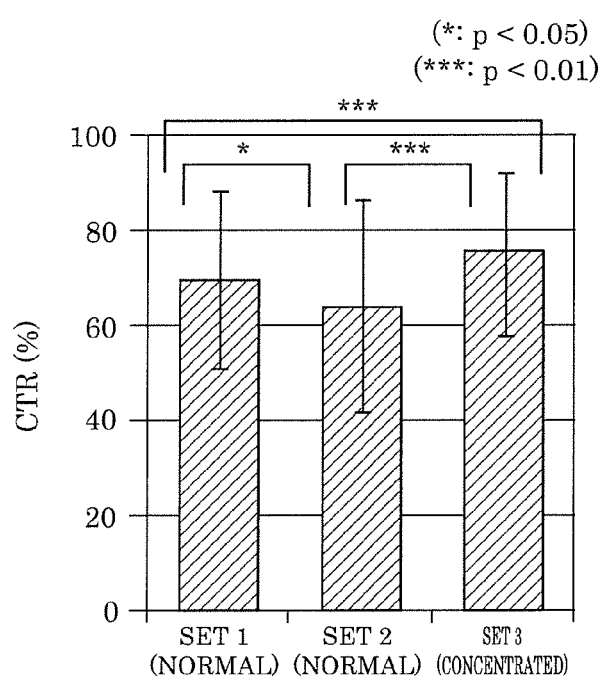
FIG. 18B illustrates a relationship between the working state of a subject and the ratio of a time of concentration.

FIG. 18A illustrates the relationship between the working states and the answer speeds of the subjects. FIG. 18B illustrates the relationship between the working states and the concentrated time ratios (CTRs) of the subjects. As shown in FIGS. 18A and 18B, three sets are performed. Two of them, set 1 and set 2 show the results of usual answer work performed by subjects 2.

In Set 3, the subjects are told as follows before answering the questions so that the concentration of subjects 2 on the answer work and the motivation of subjects 2 improve. "Now, you have only ten minutes to do the last work for today. Be concentrated on the work and do your best to proceed to answer questions accurately." That is, set 3 shows the result obtained where subjects 2 were expected to be more concentrated than in set 1 and set 2.

It is found from FIG. 18A that the answer speeds increase more in set 3 than in set 1 and set 2. As shown in FIG. 18B, the CTRs also increase more in set 3 than in set 1 and set 2. It is found that the CTRs accurately indicate the degrees of concentration.

It can be here considered that the degrees of concentration can be estimated by checking the answer speeds in the result shown in FIG. 18A. However, the answer speeds also increase depending on the degrees of skill of subjects 2.

Figure 19A:
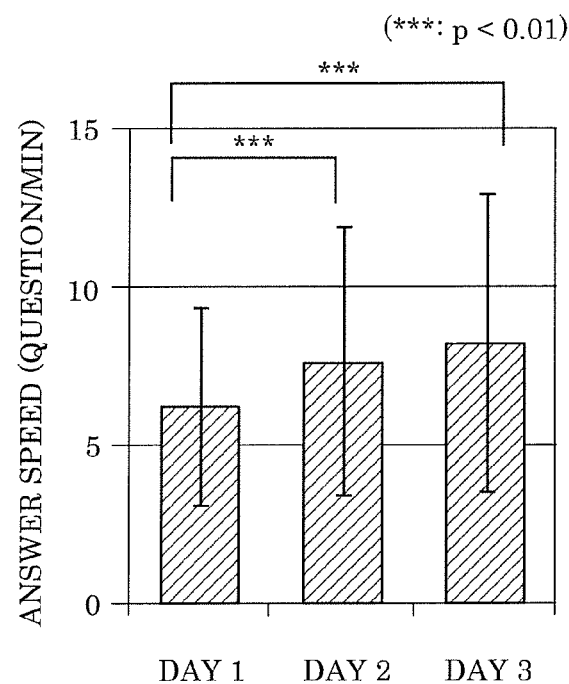
FIG. 19A illustrates a relationship between a subject's degree of skill and an answer speed.
Figure 19B:
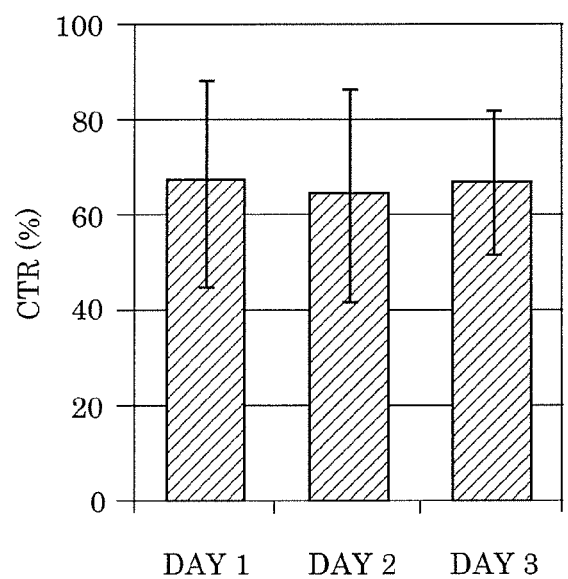
FIG. 19B illustrates a relationship between a subject's degree of skill and the ratio of a time of concentration.

FIG. 19A illustrates the relationship between the working states and the answer speeds of the subjects. FIG. 19B illustrates a relationship between the working states and the concentrated time ratios (CTRs) of the subjects. FIGS. 19A and 19B show the result of answer work for three days.

As shown in FIG. 19A, the answer speeds increase more on day 2 than on day 1 and more on day 3 than on day 2. This may be because subjects 2 becomes more skilled after repetitive answer work.

On the other hand, as shown in FIG. 19B, there is no particular change in the CTRs depending on the day. That is, it is found that the CTRs exclude the influence of the skill of the subjects and allow accurate evaluation when the subjects are concentrated. This also applies to the CDI or the MCTR in the embodiment described above.

Others

The intellectual productivity evaluation device, the intellectual productivity evaluation method, and the other aspects according to the present disclosure have been described based on the embodiment. The present disclosure is however not limited to the embodiment.

For example, an example has been described above in the embodiment where operation terminal 10 and data collection device 20 are used to automatically represent questions, receive answers from subject 2, and measure the answer times. The configuration is however not limited thereto. Specifically, intellectual productivity evaluation system 1 may exclude at least one of operation terminal 10 and data collection device 20.

For example, the plurality of questions may be presented by supplying subject 2 with paper on which the plurality of questions are printed or electric paper simply displaying the plurality of questions. In this case, subject 2 him/herself or a supervisor may measure the answer times for the respective questions and record answer time data utilizing a timer such as a stopwatch.

For example, in the embodiment described above, the distribution of the number of answers is analyzed after the parameters of curve $F_1$ of first deepest concentration and curve $F_2$ of second deepest concentration have been determined. The order is not limited thereto. Parameters $p_1$ of curve $F_1$ of first deepest concentration may be determined as the number of answers processed in the first deepest concentration. Parameter $p_2$ of curve $F_2$ of second deepest concentration may be determined as the number of answers processed in the second deepest concentration.

For example, in the embodiment described above, the cumulative distribution function of the log-normal distribution is fitted to the cumulative distribution of the answer times. The configuration is not limited thereto. As shown in FIG. 7 for example, the probability density function of the log-normal distribution may be fitted to the answer time histogram. A generally available means may be used to analyze the log-normal distribution relative to the cumulative distribution of the answer times.

In the embodiment described above, the constituent elements may be exclusive hardware or achieved by executing software programs suitable for the constituent elements. The constituent elements may be configured as a program execution unit such as a central processing unit (CPU) or a processor that reads out and executes software programs recorded in a recording medium such as a hard disk or a semiconductor memory.

At this time, the type of the processor is not particularly limited as long as providing functions by executing the programs. For example, the processor may be composed of one or more electronic circuits including a semiconductor integrated circuit such as an integrated circuit (IC) or a large-scale integration (LSI). The plurality of electronic circuits may be integrated into a single chip or mounted onto a plurality of chips. The plurality of chips may be integrated into a single device or distributed to a plurality of devices.

The present disclosure may be implemented not only by an intellectual productivity evaluation system, but also by a program and a non-transitory storage medium. The program includes, as steps, processing performed by the constituent elements of the intellectual productivity evaluation system. The non-transitory storage medium, such as a computer-readable digital versatile disc (DVD), store the program. The program may be recorded in advance in the recording medium or supplied to the recording medium via a wide area network including internet.

The comprehensive or specific aspects described above may be implemented by a system, a device, an integrated circuit, a computer program, or a computer-readable recording medium, or by a free combination of the system, the device, the integrated circuit, the computer program and the recording medium.

The method of communications between the devices described above in the embodiment are not particularly limited. Wireless communications may be established between devices by a method (or standard) of near-field communications such as ZigBee (registered trademark), Bluetooth (registered trademark), or a wireless local area network (LAN). Alternatively, the wireless communications may be established by a method (or standard) via a far-field communication network such as internet. Between the devices, the wireless communications may be replaced with wired communications. The wired communications may be, specifically, established by power line communications (PLC) or a wired LAN.

In the embodiment described above, the processing executed by a certain processing unit may be executed by another processing unit. The order of the plurality of processing may be changed. Alternatively, the plurality of processing may be executed in parallel. How to distribute the constituent elements of the intellectual productivity evaluation system to the plurality of devices has been described as an example. Instead, for example, one or more constituent elements of a certain device may be included in another device. The intellectual productivity evaluation system may be composed of a single device.

For example, the processing described above in the embodiment may be implemented by centralized processing using a single system or decentralized processing using a plurality of systems. The program may be executed by a single processor or a plurality of processors, that is, centralized processing or decentralized processing.

The present disclosure includes other embodiments, such as those obtained by variously modifying the embodiment as conceived by those skilled in the art or those achieved by freely combining the constituent elements and functions in the embodiment without departing from the scope and spirit of the present disclosure.

The invention claimed is:

1. An intellectual productivity evaluation system, comprising:
an operation terminal for causing a subject to perform a task of answering a plurality of questions as intellectual work;
an evaluation device that evaluates intellectual productivity of the subject;
one or more apparatuses that control an ambient environment of the subject; and
a timer that measures an answer time required by the subject for answering each of the plurality of questions,
wherein the operation terminal includes:
a display unit configured to present the plurality of questions to the subject; and
an input unit configured to receive an answer for each of the plurality of questions from the subject,
wherein the evaluation device includes:
an obtainment unit configured to obtain a set of answer times each of which is the answer time measured by the timer;
an evaluation unit configured to calculate an evaluation value related to a depth of concentration of the subject in a concentrated state using the set of answer times obtained by the obtainment unit, based on a model in which the subject is in the concentrated state or an unconcentrated state during the intellectual work; and
an output unit configured to determine a control detail of the one or more apparatuses using output the evaluation value calculated by the evaluation unit, and configured to output a control signal that operates the one or more apparatuses based on the control detail to provide a more concentrative environment,
wherein the concentrated state includes:
a first deepest concentration which is a mixture of a working state and a briefly interrupted state; and
a second deepest concentration which is a mixture of the working state and the briefly interrupted state and in which the subject is less deeply concentrated than in the first deepest concentration,
wherein the evaluation unit calculates, as the evaluation value, a ratio of a time of first deepest concentration in which the subject is in the first deepest concentration to a time of concentration in which the subject is in the concentrated state,
wherein the time of concentration is a sum of the time of first deepest concentration and a time of second deepest concentration in which the subject is in the second deepest concentration, and
wherein, the one or more apparatuses operate according to the control signal output from the output unit,
wherein the evaluation unit includes:
a distribution generation unit configured to generate, using the set of answer times, an answer time distribution indicating a total number of answers obtained in each of the answer times;
a fitting unit configured to fit, to the answer time distribution, a curve of first deepest concentration representing a distribution function of a log-normal distribution associated with the first deepest concentration, and a curve of second deepest concentration representing a distribution function of a log-normal distribution associated with the second deepest concentration; and
a calculation unit configured to calculate the time of first deepest concentration and the time of second deepest concentration based on the curve of first deepest concentration and the curve of second deepest concentration, respectively, and
the log-normal distribution associated with each of the first deepest concentration and the second deepest concentration is represented by using parameters $\mu$, $\sigma$ and p:

$$F(t) = \frac{p}{2} \text{erfc}\left(-\frac{\ln(t) - \mu}{\sqrt{2}\sigma}\right), \text{ where } \text{erfc}(x) = \frac{2}{\sqrt{\pi}} \int_x^\infty e^{-s^2} ds.$$

2. The intellectual productivity evaluation system according to claim 1, wherein the time of first deepest concentration is a product of the total number of answers processed in the first deepest concentration and an expected value of answer times in the first deepest concentration, and the time of second deepest concentration is a product of the total number of answers processed in the second deepest concentration and an expected value of answer times in the second deepest concentration.

3. The intellectual productivity evaluation system according to claim 2, wherein
the fitting unit fits:
the curve of first deepest concentration to a first subset of answer times shorter than a first threshold in the answer time distribution; and
the curve of second deepest concentration to a second subset of answer times shorter than a second threshold in the answer time distribution other than the first subset.

4. The intellectual productivity evaluation system according to claim 2, wherein
the curve of first deepest concentration represents a cumulative distribution function of the log-normal distribution associated with the first deepest concentration,
the curve of second deepest concentration represents a cumulative distribution function of the log-normal distribution associated with the second deepest concentration, and
the distribution generation unit sorts the set of answer times in ascending order of the answer times and smoothens the set of answer times to generate, as the answer time distribution, a distribution of the total number of cumulative answers in the answer times.

5. An intellectual productivity evaluation method, comprising: presenting, by a display unit of an operation terminal, a plurality of questions to a subject on whom a task of answering the plurality of questions is imposed as intellectual work;
receiving, by an input unit of the operation terminal, an answer to each of the plurality of question from the subject;
measuring, by a timer, an answer time required by the subject for answering each of the plurality of questions;
obtaining a set of answer times, each answer time of the set being the answer time as measured by the timer;
calculating an evaluation value related to a depth of concentration of the subject in a concentrated state using the set of answer times obtained based on a model in which the subject is in the concentrated state or an unconcentrated state during the intellectual work;
outputting a control detail for one or more apparatuses using the evaluation value calculated and a control signal that operates the one or more apparatuses based on the control detail, wherein one or more apparatuses control an ambient environment of the subject;

operating one or more apparatuses according to the control signal output to provide a more concentrative environment, wherein the concentrated state includes:
- a first deepest concentration which is a mixture of a working state and a briefly interrupted state; and
- a second deepest concentration which is a mixture of the working state and the briefly interrupted state and in which the subject is less deeply concentrated than in the first deepest concentration, wherein calculating the evaluation value includes calculating, as the evaluation value, a ratio of a time of first deepest concentration in which the subject is in the first deepest concentration to a time of concentration in which the subject is in the concentrated state, and wherein the time of concentration is a sum of the time of first deepest concentration and a time of second deepest concentration in which the subject is in the second deepest concentration;

generating, using the set of answer times, an answer time distribution indicating a total number of answers obtained in each of the answer times;

fitting, to the answer time distribution, a curve of first deepest concentration representing a distribution function of a log-normal distribution associated with the first deepest concentration, and a curve of second deepest concentration representing a distribution function of a log-normal distribution associated with the second deepest concentration; and calculating the time of first deepest concentration and the time of second deepest concentration based on the curve of first deepest concentration and the curve of second deepest concentration, respectively, and the log-normal distribution associated with each of the first deepest concentration and the second deepest concentration is represented by using parameters $\mu$, $\sigma$ and p:

$$F(t) = \frac{p}{2}\mathrm{erfc}\left(-\frac{\ln(t)-\mu}{\sqrt{2}\sigma}\right), \text{ where } \mathrm{erfc}(x) = \frac{2}{\sqrt{\pi}}\int_{x}^{\infty} e^{-s^2} ds.$$

6. A non-transitory computer-readable recording medium storing a program configured to cause a computer to execute the intellectual productivity evaluation method according to claim 5.

7. The intellectual productivity evaluation system according to claim 1, wherein the one or more apparatuses include at least one an air conditioner, a lighting system, a speaker, an aroma diffuser, and an air cleaner or a ventilator, and
when the evaluation value indicated in the evaluation value information provided by the output unit is less than a threshold,
the air conditioner reduces temperature of a space including the subject or directs air on the subject;
the lighting system improves color temperature of light illuminating the space of the subject or increases brightness of the space including the subject;
the speaker executes noise cancellation;
the aroma diffuser emits a fragrant substance exhibiting cool stimulation in the space including the subject; or
the air cleaner or a ventilator reduces particle substance concentration,
to provide a more concentrative environment.

8. The intellectual productivity evaluation system according to claim 1, wherein a number of the plurality of questions is 100 to 1000.

9. The intellectual productivity evaluation method according to claim 5, wherein a number of the plurality of questions is 100 to 1000.

10. The intellectual productivity evaluation method according to claim 5, wherein the one or more apparatuses include at least one an air conditioner, a lighting system, a speaker, an aroma diffuser, and an air cleaner or a ventilator, and
when the evaluation value indicated in the evaluation value information provided by the output unit is less than a threshold,
the air conditioner reduces temperature of a space including the subject or directs air on the subject;
the lighting system improves color temperature of light illuminating the space of the subject or increases brightness of the space including the subject;
the speaker executes noise cancellation;
the aroma diffuser emits a fragrant substance exhibiting cool stimulation in the space including the subject; or
the air cleaner or a ventilator reduces particle substance concentration,
to provide a more concentrative environment.

* * * * *